US011583537B2

(12) United States Patent
Wolf

(10) Patent No.: US 11,583,537 B2
(45) Date of Patent: Feb. 21, 2023

(54) METHODS AND SYNERGIC COMPOSITIONS FOR TREATING VIRAL INFECTIONS

(71) Applicant: HADASIT MEDICAL RESEARCH SERVICES AND DEVELOPMENT LTD., Jerusalem (IL)

(72) Inventor: Dana Wolf, Mevaseret Zion (IL)

(73) Assignee: HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 31 days.

(21) Appl. No.: 17/026,593

(22) Filed: Sep. 21, 2020

(65) Prior Publication Data
US 2021/0000839 A1 Jan. 7, 2021

Related U.S. Application Data

(63) Continuation-in-part of application No. PCT/IL2019/050303, filed on Mar. 19, 2019.

(60) Provisional application No. 62/646,397, filed on Mar. 22, 2018.

(51) Int. Cl.
| A61K 31/541 | (2006.01) |
| A61P 31/12 | (2006.01) |
| A61K 31/517 | (2006.01) |
| A61K 31/522 | (2006.01) |
| A61K 31/675 | (2006.01) |
| A61K 31/7056 | (2006.01) |

(52) U.S. Cl.
CPC .......... *A61K 31/541* (2013.01); *A61K 31/517* (2013.01); *A61K 31/522* (2013.01); *A61K 31/675* (2013.01); *A61K 31/7056* (2013.01); *A61P 31/12* (2018.01)

(58) Field of Classification Search
None
See application file for complete search history.

(56) References Cited

U.S. PATENT DOCUMENTS

| 6,306,896 | B1 | 10/2001 | Scheiwe | |
| 6,984,640 | B1* | 1/2006 | Haynes | A61K 31/5377 |
| | | | | 514/228.2 |
| 9,616,067 | B2 | 4/2017 | Haynes | |
| 10,111,884 | B2* | 10/2018 | Haynes | A61K 31/541 |
| 2008/0161324 | A1 | 7/2008 | Johansen | |

FOREIGN PATENT DOCUMENTS

| WO | 2013157005 A1 | 10/2013 |
| WO | 2019180708 A1 | 9/2019 |

OTHER PUBLICATIONS

Chou (2006) Theoretical basis, experimental design, and computerized simulation of synergism and antagonism in drug combination studies. Pharmacol Rev 58(3): 621-681.
Chou et al., (2011) The unique antiviral activity of artesunate is broadly effective against human cytomegaloviruses including therapy-resistant mutants. Antiviral Res 92(2): 364-368.
D'Alessandro et al., (2007) Differential effects on angiogenesis of two antimalarial compounds, dihydroartemisinin and artemisone: implications for embryotoxicity. Toxicology 241(1-2): 66-74.
Drouot et al., (2016) Artesunate demonstrates in vitro synergism with several antiviral agents against human cytomegalovirus. Antivir Ther 21(6): 535-539.
Dziurzynski et al., (2012) Consensus on the role of human cytomegalovirus in glioblastoma. Neuro Oncol 14(3): 246-255.
Efferth et al., (2002) Antiviral activity of artesunate towards wild-type, recombinant, and ganciclovir-resistant human cytomegaloviruses. J Mol Med (Berl) 80(4): 233-242.
He et al., (2012) Artemisinin-derived dimer diphenyl phosphate is an irreversible inhibitor of human cytomegalovirus replication. Antimicrob Agents Chemother 56(7): 3508-3515.
Ho et al., (2014) Artemisinins: pharmacological actions beyond anti-malarial. Pharmacol Ther 142(1): 126-139.
Morère et al., (2015) Ex vivo model of congenital cytomegalovirus infection and new combination therapies. Placenta 36(1): 41-47.
Nagelschmitz et al., (2008) First assessment in humans of the safety, tolerability, pharmacokinetics, and ex vivo pharmacodynamic anti-malarial activity of the new artemisinin derivative artemisone. Antimicrob Agents Chemother 52(9): 3085-3091.
Oiknine-Djian et al., (2018) The Artemisinin Derivative Artemisone Is a Potent Inhibitor of Human Cytomegalovirus Replication. Antimicrob Agents Chemother 62(7): e00288-18; 13 pages.
Oiknine-Djian et al., (2019) Artemisone demonstrates synergistic antiviral activity in combination with approved and experimental drugs active against human cytomegalovirus. Antiviral Res 172: 104639; 4 pages.
Oiknine-Djian et al., The Artemisinin Derivative Artemisone Is a Potent Inhibitor of Human Cytomegalovirus Replication and Acts Synergistically with Approved and Experimental Antiviral Drugs. Abstract presented at the ILANIT/FISEB conference Feb. 17-20, 2020, Eilat, Israel.

(Continued)

*Primary Examiner* — My-Chau T. Tran
(74) *Attorney, Agent, or Firm* — Raphael Bellum PLLC

(57) ABSTRACT

The present invention provides compositions and methods for treating, preventing, and inhibiting viral replication, viral infections and viral diseases and disorders, comprising use of artemisone in combination with at least one antiviral compound selected from maribavir, cidofovir, brincidofovir, valganciclovir, and letermovir, and the combination provides a synergistic anti-viral effect. The invention also provides compositions and methods for treating, preventing, and inhibiting viral replication, viral infections and viral diseases and disorders, comprising the use of artemisone in combination with ganciclovir, wherein the molar ratio between artemisone and ganciclovir is about 1:100 to 100:1, and the combination provides a synergistic anti-viral effect. Pharmaceutical compositions comprising artemisone and at least one of said antiviral compounds are provided as well.

16 Claims, No Drawings

(56) References Cited

OTHER PUBLICATIONS

Oiknine-Djian et al., Artemisone Is a Potent Inhibitor of Human Cytomegalovirus Replication and Acts Synergistically with Approved and Experimental Antiviral Drugs. Poster presented at the ILANIT/FISEB conference Feb. 17-20, 2020, Eilat, Israel.

Shapira et al., (2008) Artesunate as a potent antiviral agent in a patient with late drug-resistant cytomegalovirus infection after hematopoietic stem cell transplantation. Clin Infect Dis 46(9): 1455-1457.

Weisblum et al., (2011) Modeling of human cytomegalovirus maternal-fetal transmission in a novel decidual organ culture. J Virol 85(24): 13204-13213.

Weisblum et al., (2017) APOBEC3A Is Upregulated by Human Cytomegalovirus (HCMV) in the Maternal-Fetal Interface, Acting as an Innate Anti-HCMV Effector. J Virol 91(23): e01296-17; 13 pages.

Wolf et al., (1995) Mutations in human cytomegalovirus UL97 gene confer clinical resistance to ganciclovir and can be detected directly in patient plasma. J Clin Invest 95(1): 257-263.

* cited by examiner

METHODS AND SYNERGIC COMPOSITIONS FOR TREATING VIRAL INFECTIONS

CROSS-REFERENCE TO RELATED APPLICATIONS

This application is a continuation in part of International Application No. PCT/IL2019/050303, filed Mar. 19, 2019, which claims priority to U.S. Application No. 62/646,397, filed on Mar. 22, 2018, which are incorporated herein by reference.

FIELD OF THE INVENTION

The present invention is related to compositions and methods for inhibiting viral replication and treating viral infections, diseases and disorders, using artemisone in combination with at least one additional antiviral compound, when such a combination provides a synergistic antiviral effect.

BACKGROUND OF THE INVENTION

The compound artemisinin, also known as qinghaosu (III) and its derivatives have been used primarily for the treatment of malaria, as described in U.S. Pat. No. 6,306,896 to Scheiwe. Artemisone, is a derivative of artemisinin and differs from currently used clinical artemisinins in that it does not elicit neurotoxicity in preclinical in vitro and in vivo screens. In a pilot tolerability test, treatment of male rats with artemisone at 50 mg/kg for 14 days had no effect as compared to controls. Studies involving proliferation of human endothelial cells and generation of new vessels, indicate that artemisone is significantly less anti-angiogenic than dihydroartemisinin, suggesting that it might be safer to use artemisone during pregnancy (D'Alessandro et al., Toxicology, 2007, 241, 66-74). The safety of artemisone, its tolerability and pharmacokinetics were tested in Phase I clinical trial (Nagelschmitz et al., Antimicrobial agents and chemotherapy, 2008, 52(9), 3085-3091).

Viral infections account for a very large fraction of infectious disease mortality and morbidity worldwide. Cytomegalovirus (CMV), for example, is a beta herpesvirus; it is a major cause of morbidity and mortality in immunocompromised individuals including AIDS patients and recipients of hematopoietic stem cell transplantation (HSCT) or solid organ transplants, cancer patients, and patients at intensive care. CMV is also the leading cause of congenital infection, affecting ~1% of live births, with resultant neurological damage and loss of hearing. Despite the considerable public health burden of congenital CMV, no established prenatal antiviral treatments are available.

In the transplantation setting, the widespread use of preventive antiviral therapy has reduced the occurrence of early CMV disease; however, the development of late disease is increasingly recognized. Preventive antiviral strategies include (a) preemptive therapy in patients who become positive for CMV antigen or CMV DNA in the blood after transplantation and (b) universal prophylaxis initiated in all at-risk patients at the time of transplantation or engraftment and continued for a few months after transplantation.

All currently available anti-CMV drugs for systemic treatment of CMV infection, including ganciclovir, foscarnet and cidofovir, target the viral DNA polymerase. Although these drugs are effective, their use is limited by toxicity, low oral bioavailability (except valganciclovir), high cost, and teratogenicity. Additionally, prolonged or repeated antiviral treatment may lead to the development of drug resistance and occasionally cross-resistance to multiple drugs.

Artemisinin derivatives have been suggested for the treatment of viral infections. Artesunate has been shown to inhibit the replication of cytomegalovirus (CMV) (Efferth et al., J. Mol. Med., 2002, 80(4), 233-242) and has been used to treat CMV infection (Shapira et al., Clin. Infect. Dis., 2008, 46(9), 1455-1457). U.S. Pat. No. 9,616,067 suggested use of artemisone for treatment of viral infections alone or in combination with other antiviral drugs. Patent application published as US 2008/0161324 describes that artemisinins may be useful in combination with other agents in treating viral diseases. Several publication suggested combination of artesunate with other antiviral compounds (Drouot, Piret and Boivin, 2016, Antiviral Therapy; 21:535-539; Chou et al., 2011, Antiviral Research, 92: 364-368; He et al., 2012, Antimicrobial Agents and Chemotherapy, 53(7): 3508-3515). Morere et al., (Placenta 36 (2015) 41-47) showed that a synergistic effect that was observed in vitro for artesunate and maribavir was not confirmed in ex-vivo model.

There is a clear unmet need for generation of additional effective and safe anti-viral treatments.

SUMMARY OF THE INVENTION

The present invention is based in part on the unexpected observation that the combination of artemisone and an antiviral compound selected from brincidofovir, cidofovir, maribavir, and letermovir provides a synergistic antiviral effect. It was shown in particular that artemisone in combination with maribavir provides a strong synergic antiviral effect, artemisone with HCMV DNA polymerase inhibitors such as brincidofovir or cidofovir provide a synergic effect, while combination of artemisone with HCMV terminase inhibitors such as letermovir or BDCRB resulted in a moderate synergism. Combination of artemisone with ganciclovir in molar ratio of 1:1 provided a moderate synergism as well. These results were further reaffirmed in ex-vivo model showing that a combination of artemisone and maribavir provides a synergic effect. According to one aspect, the present invention provides a combination of artemisone and at least one compound selected from brincidofovir, cidofovir, maribavir, valganciclovir and letermovir, for use in treating a viral infection or disease or in suppressing viral replication, wherein said combination provides a synergistic antiviral effect. According to some embodiments, the combination for use comprises artemisone and maribavir, wherein the molar ratio of artemisone to maribavir is in the range of from 1:100 to 100:1. According to certain embodiments, the combination for use comprises artemisone and valganciclovir, wherein the molar ratio of artemisone to valganciclovir is in the range of from 1:100 to 100:1. According to a further embodiment, the combination comprises artemisone and letermovir, wherein the molar ratio of artemisone to letermovir is in the range of from 2:1 to 20000:1. According to still another embodiment, the combination comprises artemisone and brincidofovir, wherein the molar ratio of artemisone to brincidofovir is in the range of from 10:1 to $10^5$:1. According to one embodiment, the combination comprises artemisone and cidofovir, wherein the molar ratio of artemisone and cidofovir is in the range from 250:1 to 1:40. According to some embodiment, the present invention provides a combination comprising artemisone and ganciclovir for use in treating a viral infection or disease, wherein the molar ratio of artemisone to ganciclovir is in the range of from 1:100 to 100:1, and wherein said combination provides a synergistic antiviral effect. According to other embodiment, the present invention provides a combination comprising artemisone and cidofovir for use in treating a viral infection, wherein the molar ratio of artemisone to cidofovir is in the range of from 250:1 to 1:40, and wherein said combination provides a synergistic antiviral effect.

According to certain embodiments, artemisone and at least one compound selected from ganciclovir, brincidofovir, cidofovir, maribavir, valganciclovir and letermovir are administered in a sequential manner or in a substantially simultaneous manner.

According to some embodiments, the combination is formulated in a single dosage form, e.g. as a pharmaceutical composition. According to other embodiments, each one of the compounds of said combinations is formulated in a separate dosage form, e.g. in the same type of dosage form, or formulated in different dosage forms optionally configured for administration in different routes of administration and/or in different regimens.

According to some embodiments, the present invention provides a combination of artemisone at least one antiviral drug selected from HCMV DNA polymerase inhibitors, such as brincidofovir or cidofovir, and HCMV terminase inhibitor, such as letermovir or BDCRB, for use in treating a viral infection or disease or in suppressing viral replication, wherein said combination provides a synergistic antiviral effect.

The combinations of the present invention are for use in treating a viral infection or replication. According to some embodiments, the virus is a herpesvirus. In one particular embodiment, the herpesvirus is a human cytomegalovirus.

According to another aspect, the present invention provides a synergistic pharmaceutical composition comprising artemisone, at least one compound selected from ganciclovir, brincidofovir, cidofovir, maribavir, valganciclovir and letermovir, and a pharmaceutically acceptable excipient, wherein the pharmaceutical composition provides a synergistic antiviral effect upon administration. According to one embodiment, the pharmaceutical composition comprises artemisone and at least one compound selected from ganciclovir and maribavir wherein the molar ratio of artemisone to said at least one compound is in the range of from 1:100 to 100:1. According to another embodiment, the synergistic pharmaceutical composition comprises artemisone and letermovir, wherein the molar ratio of artemisone to letermovir is from 2:1 to 20000:1. According to yet another embodiment, the synergistic pharmaceutical composition comprises artemisone and brincidofovir, wherein the molar ratio of artemisone to brincidofovir is from 10:1 to $10^5$:1. According to certain embodiments, the synergistic pharmaceutical composition comprises artemisone and valganciclovir, wherein the molar ratio of artemisone to valganciclovir is in the range of from 1:100 to 100:1. According to one embodiment, the synergistic pharmaceutical composition comprises artemisone and cidofovir, wherein the molar ratio of artemisone and cidofovir is in the range from 250:1 to 1:40. The synergistic pharmaceutical composition of the present is for use in treating a viral infection or in suppressing viral replication, wherein administering said composition provides a synergistic antiviral effect. According to one embodiment, the virus is herpesvirus such as human cytomegalovirus.

According to another aspect, the present invention provides a method of treating a viral infection or of suppressing a viral replication in a subject in need thereof comprising co-administering artemisone and at least one compound selected from the group consisting of brincidofovir, cidofovir, maribavir, valganciclovir and letermovir, wherein said co-administering provides a synergistic antiviral effect. According to another embodiment, the present invention provides a method of treating a viral infection or of suppressing viral replication in a subject in need thereof comprising co-administering artemisone and ganciclovir, wherein the artemisone:ganciclovir molar ratio is in the range of from 1:100 to 100:1 and said co-administering provides a synergistic antiviral effect.

According to some embodiments, the dose of artemisone and/or of at least one the aforementioned compounds is at least 2 or at least 3 times lower than the correspondent dose of artemisone and/or said compound when administered alone.

According to another aspect, the present invention provides a kit comprising a pharmaceutical composition comprising artemisone, a pharmaceutical composition comprising at least one compound selected from the group consisting of brincidofovir, cidofovir, maribavir, valganciclovir and letermovir, and instructions for use of said compositions. According to one embodiment, the present invention provides a kit comprising a pharmaceutical composition comprising artemisone, a pharmaceutical composition comprising gancyclovir, and instructions for use of said compositions. According to one embodiment, the kit is for use in treating viral infection or disease.

DETAILED DESCRIPTION OF THE INVENTION

The present invention is based in part on the unexpected finding that administration of artemisone in combination with at least one of the following compounds: ganciclovir, BDCRB, brincidofovir, maribavir, valganciclovir and letermovir results in a synergistic antiviral activity against human cytomegalovirus (HCMV). The present invention provides a combination of artemisone with at least one antiviral compound, wherein such a combination provides a synergistic antiviral effect. The present invention provides also compositions comprising said combinations and use thereof for treatment of viral diseases.

It is a well-known fact that it is impossible to predict the effect that a combination of drug would have. Three main effects that may be observed when two or more compounds are administered together: additive effect—the most common, a synergistic effect—the effect of a combination is more than a simple summation of individual effects, and an antagonism—the effect of a combination is less than a simple summation of individual effects. As stated by Chou (*Pharmacol Rev* 58:621-681, 2006), synergism or antagonism needs to be determined, and not be predicted.

According to one aspect, the present invention provides a combination of artemisone and at least one compound selected from brincidofovir, cidofovir, maribavir, valganciclovir and letermovir, for use in treating a viral infection, wherein said combination provides a synergistic antiviral effect.

According to some embodiments, the present invention provides a combination of artemisone and ganciclovir, for use in treating a viral infection, wherein said combination provides a synergistic antiviral effect and wherein the artemisone and ganciclovir has a particular defined moral ratio, e.g. from about 1:1000 to about 1000:1, about 1:100 to about 100:1, about 1:50 to about 50:1, about 1:40 to about 40:1, about 1:30 to about 30:1, about 1:20 to about 20:1, about 1:10 to about 10:1, about 1:5 to about 5:1 or about 1:1. According to one embodiment, the artemisone: ganciclovir molar ratio is in the range of from 10:1 to 1:10. According another embodiment, the artemisone: ganciclovir molar ratio is in the range of from 8:1 to 1:8. According to a further embodiment, the artemisone: ganciclovir molar ratio is in the range of from 6:1 to 1:6. According to yet another embodiment, the artemisone: ganciclovir molar ratio is in the range of from 5:1 to 1:5 or from 4:1 to 1:3. According to one embodiment, the artemisone: ganciclovir molar ratio is in the range of from 3:1 to 1:3. According to another embodiment, the artemisone:ganciclovir molar ratio is in the range of from 2:1 to 1:2. According to one embodiment, the artemisone:ganciclovir molar ratio is 1:1.

According to some embodiments, the present invention provides a combination of artemisone and ganciclovir, for use in treating a viral infection, wherein said combination provides a synergistic antiviral effect and wherein the artemisone and ganciclovir has a particular defined weight ratio, e.g. about 1:50 to about 50:1, about 1:40 to about 40:1, about 1:30 to about 30:1, about 1:20 to about 20:1, about 1:10 to about 10:1, about 1:5 to about 5:1. According to some embodiments, the weight ratio is from 1:50 to 1:20, from 1:30 to 1:10 or from 1:20 to 1:2.

According some embodiments, the composition is for use in treating a viral infection. According to one embodiment, the composition is for use in suppressing viral replication. According to another embodiment, the composition is for use in suppressing viral spread. According to other embodiments, the composition is for use in of preventing maternal fetal transmission of the virus. According to one embodiment, the composition is for use in prevention and/or prophylaxis of viral infection. According to a further embodiment, the composition is for use in preventing and/or treating of a congenital infection.

The term "artemisone" refers to a compound 10a-(4'-(S, S-dioxothiomorpholin-1'-yl)-10-deoxo-10-dihydroartemisin, having the structure of Formula I, and pharmaceutically acceptable salt and isomers thereof. Artemisone is commercially available from Bayer AG as "BAY 44-9585". Thus, in any one of the embodiments, the combination comprises artemisone, pharmaceutically acceptable salt or isomer of artemisone of Formula I.

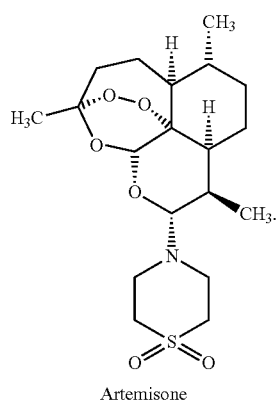

Formula I

Artemisone

The term "ganciclovir" refers to an antiviral compound having the structure represented by Formula II, a pharmaceutically acceptable salt or isomer thereof. The term "valganciclovir" refers to a prodrug of ganciclovir having the structure of Formula III, to a pharmaceutically acceptable salt or isomer thereof.

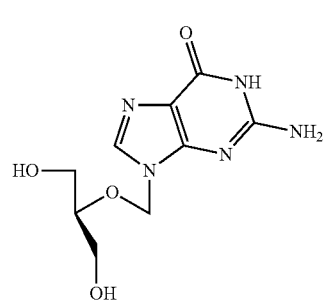

Formula II

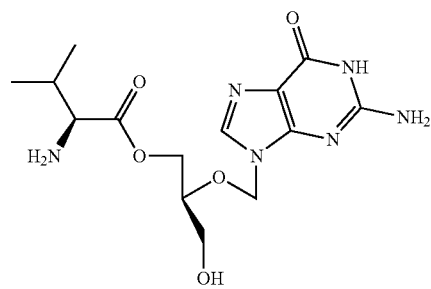

Formula III

The term "BDCRB" refers to the antiviral compound 2-bromo-5,6-dichloro-1-beta-D-ribofuranosyl benzimidazole having the structure of Formula IV and a pharmaceutically acceptable salt or isomers thereof.

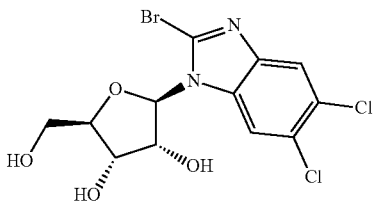

Formula IV

The term "brincidofovir" refers to a compound having the structure of Formula V and being a prodrug of an antiviral compound "cidofovir" having the structure of Formula VI, as well as to pharmaceutically acceptable salts or isomers thereof.

Formula V

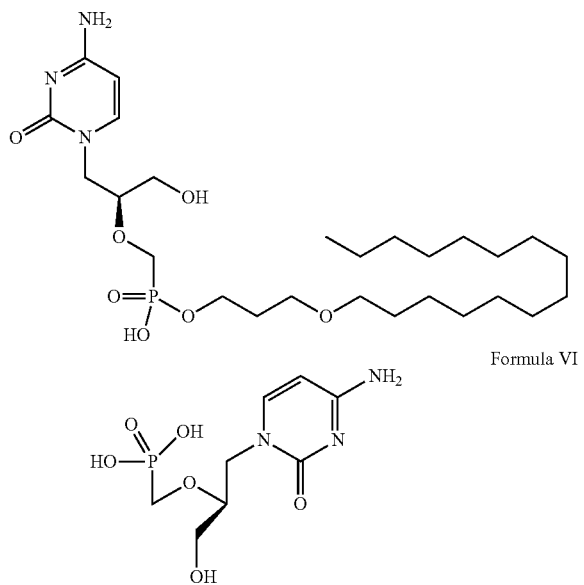

Formula VI

The term "maribavir" refers to an antiviral compound having the structure of Formula VII, pharmaceutically acceptable salts or isomers thereof.

The term "letermovir" refers to an antiviral compound having the structure of Formula VIII, pharmaceutically acceptable salts or isomers thereof.

Formula VII

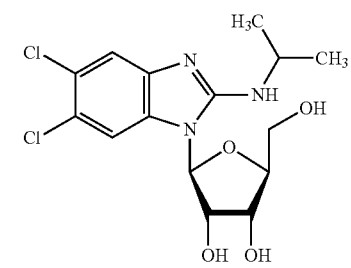

Formula VIII

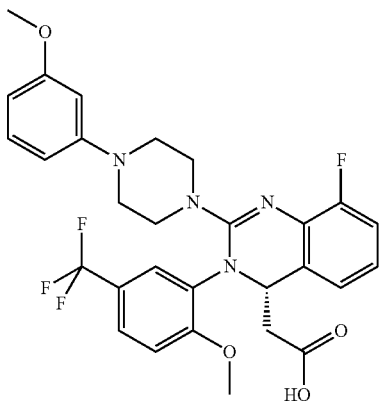

As use herein, the term "synergistic antiviral effect" means that the combination of the components of a combination exhibits greater antiviral effect or activity than the additive effect or activity provided when each component of the combination is applied alone. According to some embodiments, the synergistic effect is evaluated as described in Chou (*Pharmacol Rev* 58:621-681, 2006) and characterized by weighted average Combination Index (CIwt) value below 0.9.

CI is defined in Equation I as $$CI = \frac{(D)_1}{(D_x)_1} + \frac{(D)_2}{(D_x)_2} = \frac{1}{(DRI)_1} + \frac{1}{(DRI)_2},$$ Equation I $D_1$ and $D_2$ are the doses of the two drugs, and Dx is a dose causing to x % effect (D0.5 is $EC_{50}$). $CI_{wt}=(CI_{50}+2\times CI_{75}+3\times CI_{90}+4\times CI_{95})/10$. Thus, according to some embodiments, the combination of the present invention has a synergistic antiviral effect characterized by a CIwt value between 0.1 to 0.9, between 0.2 to 0.85, between 0.25 to 0.8, between 0.3 to 0.75, between 0.4 to 0.7, between 0.45 to 0.65 or between 0.5 to 0.6. According to another embodiment, the synergistic antiviral effect characterized by CIwt value between 0.2 to 0.5, or between 0.25 to 0.4.

The term "treating" as used herein includes the diminishment, alleviation, or amelioration of at least one symptom associated with or caused by the state, disorder or disease being treated, i.e. by a viral infection. As used herein, the term "treating viral infections" means to inhibit the replication of the particular virus, to inhibit viral transmission, to inhibit viral spread, to ameliorate or alleviate the symptoms of the disease caused by the viral infection, preventing and/or treating of a congenital infection, and/or to prevent maternal fetal transmission of the virus. The treatment is considered "therapeutic" if there is a reduction in viral load, decrease in mortality and/or morbidity. The term encompasses also the term "preventing viral infections" meaning to prevent the virus from establishing itself in the host. A treatment is considered "prophylactic" if the subject is exposed to the virus, but does not become infected with the virus as a result of treatment. In some embodiments, the term "treating" as used herein refers to the inhibition of viral replication with reduction of viral load. Accordingly, the term "treating" further encompasses prophylaxis or preemptive treatment, namely the prevention of infection and disease in yet uninfected or infected asymptomatic patients. The term further comprises treating or preventing congenital infection. According to one embodiment, the viral infection is herpesvirus infection such as human cytomegalovirus. According to some embodiments, the treated subject is a human subject. According to one embodiment, the subject is selected from the group consisting of a newborn, a pregnant woman and a transplant recipient. In one embodiment, the treatment is effected ex-vivo. The term "a therapeutically effective amount" as used herein refers to an amount of an agent which is effective, upon single or multiple dose administration to the subject in providing a therapeutic benefit to the subject. In one embodiment, the therapeutic benefit is inhibiting virus activity. Administration can be accomplished to cells or tissue cultures, or to living organisms, for example mammals, in particular humans.

According to another embodiment, the combination comprises artemisone and maribavir. According to further embodiments, the combination comprises the pharmaceutically acceptable salts and/or isomers of artemisone and/or maribavir. According to one embodiment, the molar ratio between artemisone to maribavir is in the range of from about 1:1000 to about 1000:1. According to another embodiment, the ratio between artemisone to maribavir is about 1:100 to about 100:1, about 1:50 to about 50:1, about 1:40 to about 40:1, about 1:30 to about 30:1, about 1:20 to about 20:1, about 1:10 to about 10:1, about 1:5 to about 5:1 or about 1:1. According to one embodiment, the artemisone: maribavir molar ratio is in the range of from 10:1 to 1:10. According to one embodiment, the artemisone: maribavir molar ratio is in the range of from about 2:1 to about 1:2. According to another embodiment, the artemisone: maribavir molar ratio is in the range of from about 3:1 to about 1:3. According to a further embodiment, the artemisone: maribavir molar ratio is in the range of from about 4:1 to about 1:4. According to a certain embodiment, the artemisone: maribavir molar ratio is in the range of from about 5:1 to about 1:5. According to some embodiments, the present invention provides a combination of artemisone and maribavir, for use in treating a viral infection, wherein said combination provides a synergistic antiviral effect and wherein the artemisone and maribavir has a particular defined weight ratio, e.g. about 1:50 to about 50:1, about 1:40 to about 40:1, about 1:30 to about 30:1, about 1:20 to about 20:1, about 1:10 to about 10:1, about 1:5 to about 5:1. According to some embodiments, the weight ratio of artemisone and maribavir is from 1:50 to 1:20, from 1:30 to 1:10 or from 1:20 to 1:2.

According to one embodiment, the combination comprises artemisone and BDCRB. According to further embodiments, the combination comprises the pharmaceutically acceptable salts and/or isomers of artemisone and BDCRB. According to one embodiment, the molar ratio between artemisone to BDCRB is in the range of from about 1:1000 to about 2000:1. According to another embodiment, the ratio between artemisone to BDCRB is about 1:100 to about 200:1, about 1:50 to about 100:1, about 1:10 to 20:1, 1:5 to 10:1 or 2:1. According to one embodiment, the artemisone: BDCRB molar ratio is in the range of from 20:1 to 1:10. According to another embodiment, the artemisone: BDCRB molar ratio is in the range of from 4:1 to 1:1. According to a certain embodiment, the artemisone: BDCRB molar ratio is in the range of from 6:1 to 1:2. According to one embodiment, the artemisone: BDCRB molar ratio is in the range of from 8:1 to 1:4.

According to one embodiment, the combination comprises artemisone and letermovir. According to further embodiments, the combination comprises the pharmaceutically acceptable salts and/or isomers of artemisone and letermovir. According to one embodiment, the molar ratio between artemisone and/or letermovir is in the range of from 1:5 to 200000:1. According to another embodiment, the ratio between artemisone and letermovir is in the range of from 2:1 to 20000, 4:1 to 10000:1, 20:1 to 2000:1 or 100:1 to 250:1, or 200:1 According to one embodiment, the artemisone: letermovir molar ratio is in the range of from 2000:1 to 20:1. According to another embodiment, the artemisone: letermovir molar ratio is in the range of from 600:1 to 50:1. According to one embodiment, the artemisone: letermovir molar ratio is in the range of from 400:1 to 100:1. According to yet another embodiment, the artemisone: letermovir molar ratio is in the range of from 800:1 to 25:1. According to some embodiments, the present invention provides a combination of artemisone and letermovir, for use in treating a viral infection, wherein said combination provides a synergistic antiviral effect and wherein the artemisone and letermovir has a particular defined weight ratio, e.g. about 1:50 to about 50:1, about 1:40 to about 40:1, about 1:30 to about 30:1, about 1:20 to about 20:1, about 1:10 to about 10:1, about 1:5 to about 5:1. According to some embodiments, the weight ratio of artemisone and letermovir is from 1:50 to 1:20, from 1:30 to 1:10 or from 1:20 to 1:3.

According to one embodiment, the combination comprises artemisone and brincidofovir. According to further embodiments, the combination comprises the pharmaceutically acceptable salts and/or isomers of artemisone and/or brincidofovir. According to one embodiment, the molar ratio between artemisone and brincidofovir is in the range of from 1:1 to $10^6$:1. According to another embodiment, the ratio between artemisone and brincidofovir is in the range of from 10:1 to $10^5$:1, 100:1 to $10^4$:1, 500:1 to 1500:1, or 1000:1. According to one embodiment, the artemisone: brincidofovir molar ratio is in the range of from 10000:1 to 100:1. According to another embodiment, the artemisone:brincidofovir molar ratio is in the range of from 3000:1 to 300:1. According to a further embodiment, the artemisone:brincidofovir molar ratio is in the range of from 2000:1 to 500:1. According to certain embodiments, the artemisone:brincidofovir molar ratio is in the range of from 4000:1 to 200:1.

According yet another embodiment, the combination comprises artemisone and cidofovir, or a pharmaceutically acceptable salts and/or isomers thereof. According to one embodiment, the combination comprises artemisone and cidofovir. According to one embodiment, the molar ratio between artemisone and cidofovir is in the range of from 1:1 to $10^6$:1. According to another embodiment, the ratio between artemisone and cidofovir is in the range of from 10:1 to $10^5$:1, 100:1 to $10^4$:1, 500:1 to 1500:1, or 1000:1. According to one embodiment, the artemisone:cidofovir molar ratio is in the range of from 10000:1 to 100:1. According to another embodiment, the artemisone:cidofovir molar ratio is in the range of from 3000:1 to 300:1. According to some embodiments, the artemisone:cidofovir molar ratio is in the range of from 250:1 to 1:40, from 200:1 to 1:30, from 150:1 to 1:25, from 100:1 to 1:10, from 80:1 to 1:5 from 50:1 to 1:2 or from 25:1 to 1:1. According to other embodiments, the artemisone: cidofovir molar ratio is in the range of from 25:1 to 1:4, from 20 to 1:3, from 15 to 1:2, or from 10 to 1:1. According to one embodiment, the artemisone:cidofovir molar ratio is in the range of from 8:1 to 1:4:, from 6:0 to 1:3, from 4:1 to 1:2, or from 3:1 to 1:2.

According to some embodiments, the present invention provides a combination of artemisone and valganciclovir, for use in treating a viral infection, wherein said combination provides a synergistic antiviral effect and wherein the artemisone and valganciclovir has a particular defined moral ratio, e.g. about 1:1000 to about 1000:1, about 1:100 to about 100:1, about 1:50 to about 50:1, about 1:40 to about 40:1, about 1:30 to about 30:1, about 1:20 to about 20:1, about 1:10 to about 10:1, about 1:5 to about 5:1 or about 1:1. According to one embodiment, the artemisone: valganciclovir molar ratio is in the range of from 10:1 to 1:10. According another embodiment, the artemisone: valganciclovir molar ratio is in the range of from 8:1 to 1:8. According to a further embodiment, the artemisone: valganciclovir molar ratio is in the range of from 6:1 to 1:6. According to yet another embodiment, the artemisone: valganciclovir molar ratio is in the range of from 5:1 to 1:5 or from 4:1 to 1:3. According to one embodiment, the artemisone: valganciclovir molar ratio is in the range of from 3:1 to 1:3. According to another embodiment, the artemisone: ganciclovir molar ratio is in the range of from 2:1 to 1:2. According to some embodiments, the present invention provides a combination of artemisone and valganciclovir, for use in treating a viral infection, wherein said combination provides a synergistic antiviral effect and wherein the artemisone and valganciclovir has a particular defined weight ratio, e.g. about 1:50 to about 50:1, about 1:40 to about 40:1, about 1:30 to about 30:1, about 1:20 to about 20:1, about 1:10 to about 10:1, about 1:5 to about 5:1. According to some embodiments, the weight ratio of artemisone and valganciclovir is from 1:50 to 1:20, from 1:30 to 1:10 or from 1:20 to 1:3.

According to any one of the above embodiments, the relation between the doses of artemisone and at least one compound selected from ganciclovir, BDCRB, brincidofovir, cidofovir, valganciclovir, maribavir and letermovir may be presented by the ratio of their $EC_{50}$ or $IC_{50}$. Thus according to some embodiments, the present invention provides a combination of artemisone and at least one compound selected from ganciclovir, BDCRB, brincidofovir, cidofovir, valganciclovir, maribavir and letermovir, wherein artemisone and said at least one compound are administered in a doses such that the $EC_{50}$ ratio of artemisone and said compound is in the range of from 20:1 to 1:20, from 15:1 to 1:15 or from 10:1 to 1:10. According to one embodiment, the $EC_{50}$ ratio is in the range of 12:1 to 1:12, 8:1 to 1:8 or 5:1 to 1:5. According to one embodiment, the $EC_{50}$ ratio is in the range of from 3:1 to 1:3.

According to some embodiments, the combination, i.e. artemisone and at least one compound selected from ganciclovir, BDCRB, brincidofovir, cidofovir, valganciclovir, maribavir and letermovir is administered in a sequential manner. According to one embodiment, the combination of artemisone and ganciclovir is administered in a sequential manner. According to another embodiment, the combination of artemisone and BDCRB is administered in a sequential manner. According to a further embodiment, the combination of artemisone and brincidofovir is administered in a sequential manner. According to another embodiment, the combination of artemisone and valganciclovir is administered in a sequential manner. According to another embodiment, the combination of artemisone and cidofovir is administered in a sequential manner. According to one embodiment, the combination of artemisone and maribavir is administered in a sequential manner. According to another embodiment, the combination of artemisone and letermovir is administered in a sequential manner. The term "sequential manner" refers to an administration of two compounds at a different times, and optionally in different modes of administration. The agents can be administered in a sequential manner in either order. According to some embodiments, the administration comprise administering individual compositions under separate, optionally different, schedules.

According to some embodiment, the combination is administered in a substantially simultaneous manner. The terms "substantially simultaneous manner" and "simultaneous manner" refers to administration of two compounds with only a short time interval between them and may be used interchangeably. In some embodiments, the time interval is in the range of from 0.01 to 60 minutes. According to one embodiment, artemisone and at least one compound selected from BDCRB, brincidofovir, cidofovir, valganciclovir, maribavir and letermovir are administered sufficiently close in time to have the desired effect. According to another embodiment, artemisone and maribavir are administered simultaneously. According to another embodiment, artemisone and ganciclovir having the molar ratio of about 1:1000 to about 1000:1 or 1:100 to 100:1 are administered sufficiently close in time to have the desired effect. According to one embodiment, artemisone and ganciclovir having the molar ratio of about 1:10 to about 10:1. The term encompasses administration in a single dosage form. According to alternative embodiments, the term encompasses also administration in separate dosage forms. According to yet another embodiment, the term encompasses administration in different dosage forms. According to one embodiment, the term encompasses administration in different routes of administration.

According to other embodiments, the combination is administered in a simultaneous manner, i.e. the compounds are administered at the same time. According to one embodiment, artemisone and at least one compounds selected from ganciclovir, BDCRB, brincidofovir, cidofovir, valganciclovir, maribavir and letermovir are each formulated as a separated dosage form. According to such embodiments, the dosage forms are pharmaceutical compositions. According to another embodiment, the combination is formulated in a single dosage form. According to such embodiment, the combination is formulated as a pharmaceutical composition comprising artemisone and at least one compound selected from ganciclovir, BDCRB, brincidofovir, cidofovir, maribavir, valganciclovir and letermovir, and a pharmaceutically acceptable excipient.

According to some embodiments, the dosage form or the pharmaceutical composition is selected from the group consisting of tablets, pills, capsules, pellets, granules, powders, lozenges, sachets, cachets, elixirs, suspensions, dispersions, emulsions, solutions, syrups, aerosols, ointments, soft and hard gelatin capsules, suppositories, sterile injectable solutions, and sterile packaged powders.

According to other embodiment, the dosage form or the pharmaceutical composition is suitable for administration via any known route of administration. According to one embodiment, the dosage form is suitable for administration via a route selected from the group consisting of oral, rectal, intramuscular, subcutaneous, intravenous, intraperitoneal, intranasal, intraarterial, intravesicle, intraocular, transdermal and topical.

According to some embodiment, the pharmaceutical composition of the present invention is formulated as a composition for oral administration, e.g. in a form of tablets or capsules. According to other embodiments, the pharmaceutical composition of the present invention is formulated as a composition for parenteral administration. According to one embodiment, the parenteral administration is intravenous (IV) administration. According to another embodiment, the parenteral administration is intramuscular administration (IM). According to some embodiments, the composition for parenteral administration are formulated as a sterile composition for injection, e.g. in a form of a solution or a suspension.

According to the teaching of the present invention, the use of the combination comprises administration of artemisone and at least one compound selected from ganciclovir, BDCRB, brincidofovir, cidofovir, maribavir, valganciclovir and letermovir. According to one embodiment, the administration is performed in a regimen selected from a single combined composition, separate individual compositions administered substantially simultaneously, and separate individual compositions administered under separate schedules or sequentially. According to some embodiment, each antiviral compound is administered in an individual dosage form and in an administration regimens which are may be different from and non-related to each other. Each possibility represents a separate embodiment of the present invention.

The term "administering" or "administration of" a compound or a combination to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

According to some embodiments, the invention provides a combination of artemisone and at least one compound selected from BDCRB, brincidofovir, cidofovir, maribavir, valganciclovir and letermovir, for use in treating a viral infection, wherein said combination provides a synergistic antiviral effect upon administration. According to other embodiments, the invention provides a combination of artemisone and at least one compound selected from BDCRB, brincidofovir, cidofovir, maribavir, valganciclovir and letermovir, for use in suppressing viral replication, wherein said combination provides a synergistic antiviral effect upon administration. According to certain embodiments, the invention provides a combination of artemisone and at least one compound selected from BDCRB, brincidofovir, cidofovir, maribavir, valganciclovir and letermovir, for use in suppressing or inhibiting viral spread, wherein said combination provides a synergistic antiviral effect upon administration. According to another embodiment, the invention provides a combination of artemisone and ganciclovir having the molar ratio of about 1:1000 to about 1000:1, 1:100 to about 100:1, 1:10 to about 10:1, or 1:5 to about 5:1, for use in treating a viral infection or in suppressing viral replication, wherein said combination provides a synergistic antiviral effect upon administration. According to one embodiment, the present invention provides a combination of artemisone and maribavir, for use in treating a viral infection or in suppressing viral replication, wherein said combination provides a synergistic antiviral effect upon administration. According to one embodiment, the composition is for use in treating a viral infection. According to another embodiment, the composition is for use in suppressing viral replication. According to another embodiment, the composition is for use in suppressing viral spread. According to a further embodiment, the composition is for use in preventing viral infection. According to one embodiment, the infection is a congenital infection. According to some embodiment, the efficacy of the treatment is assessed by measurements of viral load, e.g. in peripheral blood in body fluids or in tissues.

According to some embodiment, the antiviral effect of the combination of artemisone and a compound selected from BDCRB, brincidofovir, cidofovir, maribavir, valganciclovir and letermovir is at least 1.1 at least 1.5 or at least 2 times higher than the calculated additive effect of the combination. According to another embodiment, the antiviral effect of the combination is at least 3, 4, 5, 6, 7, 8, 9 or 10 times higher than the calculated additive effect of the combination. According to some embodiments, the daily administered dose of said at least one compound selected from ganciclovir, BDCRB, brincidofovir, cidofovir, maribavir, valganciclovir and letermovir in said combination is lower than the standard daily dose of said compound. According to one embodiment, the daily administered dose of said at least one compound is at least 2, at least 3, at least 4, at least 5, at least 6 at least 8, at least 10, at least 20 or at least 50 times lower than the standard daily dose of said compound. According to another embodiment, the daily administered dose of artemisone is at least 1.5, at least 2, at least 3, at least 4, at least 5, at least 6 at least 8, at least 10, at least 20 or at least 50 times lower than the standard daily antiviral dose of artemisone. According to a further embodiment, the daily administered dose of said at least one compound is at least 1.5, at least 2, at least 3, at least 4, at least 5, at least 6 at least 8, at least 10, at least 20 or at least 50 times lower than the standard daily dose of said compound and the daily administered dose of artemisone is at least 1.5, at least 2, at least 3, at least 4, at least 5, at least 6 at least 8, at least 10, at least 20 or at least 50 times lower than the standard daily antiviral dose of artemisone. According to one embodiment, the dose of artemisone and/or of said at least one compound is at least 2 times lower than the concentration required for obtaining the same antiviral affect if artemisone or said at least one compound is administered alone. i.e. as a sole anti-viral agent. According to another embodiment, the dose of said at least one compound in the combination of the present invention is at least 2, at least 3, at least 4, at least 5, at least 6 at least 8, at least 10, at least 20 or at least 50 times lower than the concentration required for obtaining the same antiviral affect if said at least one compound is administered alone, and/or the dose of artemisone in said composition is at least 2, at least 3, at least 4, at least 5, at least 6 at least 8, at least 10, at least 20 or at least 50 times lower than the dose required for obtaining the same antiviral effect if artemisone is administered alone.

According to another embodiment, the dose of artemisone and at least one antiviral compound selected from ganciclovir, BDCRB, brincidofovir, cidofovir, maribavir and letermovir is determined according to the DRIs of these compound in the synergic combination considering the desired antiviral effect.

The terms "dose reduction index" and "DRI" measures the fold of dose reduction of each drug in the combination at a given effect level compared with the doses of each drug when administered alone, as a single therapy. As such DRI of 3 for each one of the drugs in the synergic combination means that in order to obtain a particular level of effect, the concentration of each one of the drugs in the combination may be reduced 3 folds in comparison to the concentration of these drugs when each drug is administered alone.

According to one embodiment, for a combination of artemisone and ganciclovir, the DRI of artemisone is from about 7 to about 16 and the DRI of ganciclovir is from about 1.97 to about 2.2 for affecting 90-97% of viruses. According to one embodiment, the dose of artemisone in the combination of artemisone and ganciclovir is from 2 to 16 times lower than the correspondent standard dose of artemisone. According to one embodiment, the dose of artemisone is 2, 3, 4, 5, 6, 7, 8, 9 or 10 times lower than the correspondent standard dose of artemisone. According to another embodiment, the dose of ganciclovir is from about 1.5 to about 2 times lower than the correspondent standard dose of ganciclovir. According to a further embodiment, the dose of artemisone is from 2 to 15 times lower than the correspondent standard dose of artemisone and the dose of ganciclovir is up to 2 times lower than the correspondent standard dose of ganciclovir when administered in combination. The suggested oral dose of artemisone is from 80 to 400 mg/day. According to one embodiment, the dose of artemisone in the combination is from 80 to 250 mg/day. According to some embodiments, the administered oral dose of artemisone in the combination is from 50 to 125 200, 60 to 175, 70 to 150 or 80 to 125 mg/day. According to another embodiment, the dose of artemisone in the combination is from 10 to 100, from 10 to 90, from 20 to 90, from 30 to 80 or, from 40 to 60 mg/day. According to one embodiment, the suggested IV dose of artemisone is 2 to 5 mg/kg/day. According to some embodiments, the IV dose of artemisone in the combination is from 0.2 to 2 from 0.3 to 1.9, from 0.4 to 1.6 from 0.5 to 1.4 from 0.6 to 1.2 or from 0.8 to 1 mg/kg/day. According to another embodiment, the IV dose of artemisone in the combination is from 0.5 to 4, from 0.7 to 3.5 from 0.8 to 3, of from 1 to 2.5 mg/kg/day. According to some embodiments, the IV dose of ganciclovir is from 1.25 to 5 mg/kg/day. According to one embodiment, the use comprises orally administering of from 50 to 125 mg/day of artemisone and IV administration of from 1.25 to 5 mg/kg/day of ganciclovir. According to another embodiment, the use comprises IV administering of from 0.2 to 2 mg/kg/day of artemisone and IV administration of from 1.25 to 5 mg/kg/day or 1.25 to 2.5 mg/kg/day of ganciclovir. According to some embodiments, artemisone is administered IV. Ganciclovir may also be administered orally, typically in a dose of 3000 mg/day. According to one embodiment, the use comprises administering ganciclovir orally from 1500 to 2500 mg/day or from 1700 mg to 2300 mg/day. According to some embodiments, the orally administered dose of artemisone in the combination is from 50 to 125 mg/day and oral dose of ganciclovir is from 1500 to 2500 mg/day.

According to a further embodiment, the dose of artemisone in the combination of artemisone and valganciclovir is from 2 to 15 times lower than the correspondent standard dose of artemisone and the dose of valganciclovir is at least 1.5 times lower than the correspondent standard dose of valganciclovir. According to one embodiment, the oral dose of artemisone in the combination is from 80 to 250 mg/day. According to some embodiments, the orally administered dose of artemisone in the combination is from 50 to 125 200, 60 to 175, 70 to 150 or 80 to 125 mg/day. According to another embodiment, the oral dose of artemisone in the combination is from 10 to 100, from 10 to 90, from 20 to 90, from 30 to 80 or, from 40 to 60 mg/day. According to one embodiment, the suggested dose of artemisone is 2 to 5 mg/kg/day. According to some embodiments, the IV dose of artemisone in the combination is from 0.2 to 2 from 0.3 to 1.9, from 0.4 to 1.6 from 0.5 to 1.4 from 0.6 to 1.2 or from 0.8 to 1 mg/kg/day. According to another embodiment, the IV dose of artemisone in the combination is from 0.5 to 4, from 0.7 to 3.5 from 0.8 to 3, of from 1 to 2.5 mg/kg/day. Valganciclovir may be administered orally, typically in a dose of 900 to 1800 mg/day. According to one embodiment, the use comprises administering valganciclovir orally from 500 mg/day to 1000 mg/day or from 700 mg/day to 900 mg/day. According to another embodiment, the use comprises administering valganciclovir orally from 500 mg/day to 1800 mg/day, from 700 mg/day to 1600 mg/day, from 800 to 1500 or from 900 to 1200 mg/day. According to some embodiments, the orally administered dose of artemisone in the combination is from 50 to 125 mg/day and oral dose of valganciclovir is from 700 to 900 mg/day. According to other embodiments, the orally administered dose of artemisone in the combination is from 50 to 125 mg/day and oral dose of valganciclovir is from 700 to 1500 mg/day.

According to another embodiment, for a combination of artemisone and maribavir, the DRI of artemisone is from about 29 to about 41 and the DRI of maribavir is from about 12.9 to about 20.6 for affecting 90-97% of viruses. According to another embodiment, for a combination of artemisone and maribavir, the DRI of artemisone is from about 5.8 to about 15 and the DRI of maribavir is from about 1.3 to about 1.5 for affecting 90-97% of viruses. According to one embodiment, the dose of artemisone in the combination of artemisone and maribavir is from 2 to 40 times lower than the standard dose of artemisone. According to some embodiments, the dose of artemisone is from 1.5 to 30 from 4 to 20 from 5 to 15 or from 7 to 10 times lower that the standard dose of artemisone. According to other embodiments, the dose of artemisone is from 1.5 to 30 from 2.5 to 12, from 3 to 10, from 3.5 to 8, or from 4 to 6 times lower that the standard dose of artemisone. According to one embodiment, the dose of artemisone is 2, 3, 4, 5, 6, 7, 8, 9 or 10 times lower that the standard dose of artemisone. According to another embodiment, the dose of maribavir is from about 1.2 to about 20 times lower than the standard dose of maribavir. According to a further embodiment, the dose of maribavir is from about 3 to about 18, from 4 to 16, from 5 to 15, or from 8 to 12 times lower than the standard dose of maribavir. According to one embodiment, the dose of maribavir is 2, 3, 4, 5, 6, 7, 8, 9 or 10 times lower that the standard dose of maribavir. According to another embodiment, the dose of maribavir is from about 1.2 to about 1.5 times lower than the standard dose of maribavir. According to a further embodiment, the dose of artemisone is from 2 to 20 times lower than the correspondent standard dose of artemisone and the dose of maribavir is from 2 to 20 times lower than the correspondent standard dose of maribavir when administered in combination. According to a further embodiment, the dose of artemisone is from 1.5 to 15 times lower than the correspondent standard dose of artemisone and the dose of maribavir is from 1.2 to 1.5 times lower than the correspondent standard dose of maribavir when administered in combination. The suggested dose of artemisone is from 80 to 400 mg/day. According to one embodiment, the dose of artemisone in the combination of artemisone and maribavir is from 80 to 250 mg/day. According to some embodiments, the orally administered dose of artemisone in the combination is from 50 to 200, 60 to 175, 70 to 150 or 80 to 125 mg/day. According to another embodiment, the oral dose of artemisone in the combination is from 10 to 100, from 10 to 90, from 20 to 90, from 30 to 80 or, from 40 to 60 mg/day. According to some embodiments, the IV dose of artemisone in the combination is from 0.2 to 2 from 0.3 to 1.9, from 0.4 to 1.6 from 0.5 to 1.4 from 0.6 to 1.2 or from 0.8 to 1 mg/kg/day. According to another embodiment, the IV dose of artemisone in the combination is from 0.5 to 4, from 0.7 to 3.5 from 0.8 to 3, of from 1 to 2.5 mg/kg/day. The commonly used dose of maribavir is from 200 to 2400 mg/day orally. According to one embodiment, the use comprises administration of a combination of artemisone and maribavir, wherein the dose of maribavir is from 100 to 2400, from 150 to 2000 mg/day, or from 700 to 900 mg/day. According to other embodiment, the dose the oral dose of artemisone in combination of artemisone and maribavir is from is from 80 to 250 mg/day and the dose of maribavir is from 150 to 2000 mg/day or from 700 to 900 mg/day. According to a further embodiment, the dose the oral dose of artemisone in combination of artemisone and maribavir is from is from 80 to 150 mg/day and the dose of maribavir is from 100 to 1000 mg/day or from 80 to 800 mg/day.

According to another embodiment, for a combination of artemisone and letermovir, the DRI of artemisone is from about 7 to about 16.5 and the DRI of letermovir is from about 1.7 to about 2.36 for affecting 90-97% of viruses.

According to one embodiment, the dose of artemisone in the combination of artemisone and letermovir is from 2 to 16 times lower than the corresponding standard dose of artemisone. According to some embodiments, the dose of artemisone is from 3 to 15, from 4 to 12 or from 5 to 10 times lower that the correspondent standard dose of artemisone. According to one embodiment, the dose of artemisone is 2, 3, 4, 5, 6, 7, 8, 9 or 10 times lower that the standard dose of artemisone. According to another embodiment, the dose of letermovir is from about 1.5 to about 2 times lower than the correspondent standard dose of letermovir. According to a further embodiment, the dose of artemisone is from 2 to 16 times lower than the correspondent standard dose of artemisone and the dose of letermovir is about 2 lower the correspondent standard dose of letermovir when administered in combination. According to one embodiment, the dose of artemisone in the combination of artemisone and letermovir is from is from 80 to 250 mg/day. According to some embodiments, the orally administered dose of artemisone in the combination is from 50 to 125 200, 60 to 175, 70 to 150 or 80 to 125 mg/day. According to another embodiment, the oral dose of artemisone in the combination is from 10 to 100, from 10 to 90, from 20 to 90, from 30 to 80 or, from 40 to 60 mg/day. According to some embodiments, the IV dose of artemisone in the combination is from 0.2 to 2 from 0.3 to 1.9, from 0.4 to 1.6 from 0.5 to 1.4 from 0.6 to 1.2 or from 0.8 to 1 mg/kg/day. According to another embodiment, the IV dose of artemisone in the combination is from 0.5 to 4, from 0.7 to 3.5 from 0.8 to 3, of from 1 to 2.5 mg/kg/day. The typical dose of letermovir is from 240 to 480 mg/day, orally. In the combination of artemisone and letermovir, the dose of letermovir is from 120 to 450 mg/day, from 140 to 400 mg/day, from 180 to 350 mg/day or from 200 to 300 mg/day. According to one embodiment, the dose of artemisone in the combination is from 50 to 125 mg/day and the dose of the dose of letermovir is from 180 to 300 mg/day.

According to another embodiment, for a combination of artemisone and brincidofovir, the DRI of artemisone is from about 7.1 to about 19 and the DRI of brincidofovir is from about 1.3 to about 1.6 for affecting 90-97% of viruses. According to one embodiment, the dose of artemisone in the combination of artemisone and brincidofovir is from 2 to 18 times lower than the standard dose of artemisone. According to some embodiments, the dose of artemisone is from 3 to 15, from 4 to 12 or from 5 to 10 times lower that the standard dose of artemisone. According to one embodiment, the dose of artemisone is 2, 3, 4, 5, 6, 7, 8, 9 or 10 times lower that the standard dose of artemisone. According to another embodiment, the dose of brincidofovir is from about 1.5 to about 2 lower than the standard dose of brincidofovir. The dose of artemisone is from 80 to 400 mg/day. According to one embodiment, the dose of artemisone in combination of artemisone and brincidofovir is from 100 to 250 mg/day. According to some embodiments, the administered dose of artemisone in the combination is from 50 to 200, 60 to 175, 70 to 150 or 80 to 125 mg/day. According to another embodiment, the dose of artemisone in the combination is from 10 to 100, from 10 to 90, from 20 to 90, from 30 to 80 or, from 40 to 60 mg/day. According to one embodiment, the typical dose of artemisone is 2 to 5 mg/kg/day. According to some embodiments, the dose of artemisone in the combination is from 0.2 to 2 from 0.3 to 1.9, from 0.4 to 1.6 from 0.5 to 1.4 from 0.6 to 1.2 or from 0.8 to 1 mg/kg/day. Typical dose of oral brincidofovir is 100 mg once or twice a week. According to some embodiments, the dose in the combination is reduced up to 1.5 or up to 2 times and/or addition administration regimen are contemplated such as daily administration.

According to another embodiment, for a combination of artemisone and cidofovir, the DRI of artemisone is from about 8 to about 18 and the DRI of cidofovir is from about 2.5 to about 3.2 for affecting 90-97% of viruses. According to one embodiment, the dose of artemisone in the combination of artemisone and cidofovir is from 2 to 18 times lower than the corresponding standard dose of artemisone. According to some embodiments, the dose of artemisone is from 3 to 15, from 4 to 12 or from 5 to 10 times lower that the correspondent standard dose of artemisone. According to one embodiment, the dose of artemisone is 2, 3, 4, 5, 6, 7, 8, 9 or 10 times lower that the standard dose of artemisone. According to another embodiment, the dose of cidofovir is from about 2 to about 3 times lower than the correspondent standard dose of cidofovir. According to a further embodiment, the dose of artemisone in the combination is from 2 to 16 times lower than the correspondent standard dose of artemisone and the dose of cidofovir in the combination is from about 2 to about 3 times lower than the correspondent standard dose. According to one embodiment, the dose of artemisone in the combination of artemisone and cidofovir is from is from 80 to 250 mg/day. According to some embodiments, the orally administered dose of artemisone in the combination is from 50 to 125 200, 60 to 175, 70 to 150 or 80 to 125 mg/day. According to another embodiment, the oral dose of artemisone in the combination is from 10 to 100, from 10 to 90, from 20 to 90, from 30 to 80 or, from 40 to 60 mg/day. According to some embodiments, the IV dose of artemisone in the combination is from 0.2 to 2 from 0.3 to 1.9, from 0.4 to 1.6 from 0.5 to 1.4 from 0.6 to 1.2 or from 0.8 to 1 mg/kg/day. According to another embodiment, the IV dose of artemisone in the combination is from 0.5 to 4, from 0.7 to 3.5 from 0.8 to 3, of from 1 to 2.5 mg/kg/day. The typical dose of cidofovir is about 5 mg/kg/week IV. In the combination of artemisone and cidofovir, the dose of cidofovir is from 2.5 to 4 mg/kg/week. Other regimens may be used.

The combination of the present invention is for use in treating a viral infection. According to another embodiment, the combination of the present invention is for use in suppressing viral replication. According to one embodiment, wherein said viral infection or replication is a herpesvirus infection or replication. According to some embodiments, the herpesvirus is selected from the group consisting of herpes simplex virus (HSV) type 1, HSV type 2, varicella-zoster virus, cytomegalovirus, Epstein-Barr virus (EBV), human herpesvirus 6, human herpesvirus 7, and human herpesvirus 8 (Kaposi's Sarcoma associated Herpes Virus). Each possibility represents a separate embodiment of the present invention. Human herpesvirus 6 as used herein encompasses both variants A and B. Each possibility represents a separate embodiment of the present invention. In another embodiment, the viral infection is an alpha herpesvirus infection. In certain embodiments, the viral infection is a beta herpesvirus infection. In another embodiment, the viral infection is a gamma herpesvirus infection. In yet another embodiment, the viral infection is a cytomegalovirus infection. In an exemplary embodiment, the viral infection is a human cytomegalovirus infection. In another embodiment, the viral infection is a flavivirus infection. In specific embodiments, the flavivirus infection is Bovine Viral Diarrhea virus (BVDV) infection. In other embodiments, the viral infection is hepatitis B virus (HBV) infection or hepatitis C virus (HCV) infection. Each possibility represents a separate embodiment of the present invention.

According to one embodiments, the herpesvirus is cytomegalovirus (CMV). In one particular embodiment, the CMV is a human CMV (HCMV). Thus, in one embodiment, the present invention provides a combination of artemisone and at least one compound selected from ganciclovir, BDCRB, brincidofovir, cidofovir, maribavir, valganciclovir and letermovir, for use in treating HCMV infection, wherein said combination provides a synergistic antiviral effect. According to another embodiment, the present invention provides a combination of artemisone and at least one compound selected from ganciclovir, BDCRB, brincidofovir, cidofovir, maribavir, valganciclovir and letermovir, for use in suppressing HCMV replication, wherein said combination provides a synergistic antiviral effect. In one embodiment, the present invention provides a combination of artemisone and ganciclovir for use in treating HCMV infection, wherein said combination provides a synergistic antiviral effect. In another embodiment, the present invention provides a combination of artemisone and maribavir for use in treating HCMV infection, wherein said combination provides a synergistic antiviral effect. In yet another embodiment, the present invention provides a combination of artemisone and valganciclovir for use in treating HCMV infection, wherein said combination provides a synergistic antiviral effect. According to such embodiments, the molar, weight or $EC_{50}$ ratio of artemisone to said compound is as described hereinabove.

It will be understood by those skilled in the art that the combinations and methods of the present invention have utility for treating not only viral infections themselves, but also diseases and disorders engendered by viral infections. Thus, for example, the present invention provides a method of treating a viral infection having oncomodulatory activity on a tumor in a subject in need thereof comprising administering to said subject the combination or the pharmaceutical composition of the present invention.

For example, there is some evidence that HCMV could modulate the malignant phenotype in glioblastomas, where HCMV sequences and viral gene expression exist in most, if not all, malignant gliomas (Dziurzynski et al., 2012, Neuro-Oncology, doi:10.1093/neuonc/nor227). Thus, according to some embodiments, the present invention provides a method of treating a viral infection having oncomodulatory activity on a tumor, in particular glioblastoma associated with cytomegalovirus in a subject in need thereof, the method comprising administering to said subject the combination or the pharmaceutical composition of the present invention.

Further encompassed by the present invention is the treatment of CMV infection, wherein the CMV is associated with a tumor such as, but not limited to, colon cancer, prostate cancer and the like, and the treatment of EBV, wherein the EBV is associated with a tumor such as, but not limited to, Burkitt's lymphoma, Hodgkin's lymphoma, post transplantation lympho-proliferative disorder (PTLD), and nasopharyngeal carcinoma. Each possibility represents a separate embodiment of the present invention.

It will also be understood by those skilled in the art that the combinations of the present invention are useful for prevention, attenuation or treatment and control of viral infection and disease in humans and animals. In some embodiments, the treatment is effective in cases of congenital infection. In additional embodiments, the treatment is effective in cases of CMV infection in immunosuppressed patients including transplantation recipients. In particular embodiments the treatment is effective ex-vivo. Within the scope of the present invention is the treatment of newborns that are infected with HCMV, pregnant women who are infected with HCMV, and transplantation recipients. Each possibility represents a separate embodiment of the present invention.

According to one embodiment, the present invention provides a combination of artemisone and maribavir, for use in treating HCMV, wherein the combination provides a synergistic anti-HCMV effect and wherein the administered doses of artemisone and maribavir are such that artemisone: maribavir $EC_{50}$ ratio is from 1:10 to 10:1. According to some embodiments, the artemisone:maribavir weight ratio is from 1:40 to 1:5 and/or the artemisone:maribavir molar ratio is from 10:1 to 1:10. According to one embodiment, the combination is orally administered. According to a further embodiment, the dose the oral dose of artemisone in combination of artemisone and maribavir is from is from 50 to 200 mg/day and the dose of maribavir is from 100 to 1800 mg/day or from 150 to 1200 mg/day.

According to one embodiment, the present invention provides a combination of artemisone and valganciclovir, for use in treating HCMV, wherein the combination provides a synergistic anti-HCMV effect and wherein the administered doses of artemisone and valganciclovir are such that artemisone: valganciclovir $EC_{50}$ ratio is from 1:10 to 10:1. According to some embodiments, the artemisone:valganciclovir weight ratio is from 1:40 to 1:10 and/or the artemisone: valganciclovir molar ratio is from 10:1 to 1:10. According to one embodiment, the combination is orally administered. According to other embodiments, the orally administered dose of artemisone in the combination is from 50 to 200 mg/day and oral dose of valganciclovir is from 700 to 1500 mg/day.

According to one embodiment, the present invention provides a combination of artemisone and letermovir, for use in treating HCMV, wherein the combination provides a synergistic anti-HCMV effect and wherein the administered doses of artemisone and valganciclovir are such that artemisone:letermovir $EC_{50}$ ratio is from 1:10 to 10:1. According to some embodiments, the artemisone:letermovir weight ratio is from 1:40 to 1:10 and/or the artemisone:letermovir molar ratio is from 10:1 to 1:10. According to one embodiment, the combination is orally administered. According to one embodiment, the dose of artemisone in the combination is from 50 to 20 mg/day and the dose of the dose of letermovir is from 180 to 300 mg/day.

According to another aspect, the present invention provides a synergistic pharmaceutical composition comprising: artemisone, at least one compound selected from ganciclovir, BDCRB, brincidofovir, cidofovir, maribavir, valganciclovir and letermovir, and a pharmaceutically acceptable excipient. According to some embodiments, the pharmaceutical composition provides a synergistic antiviral effect. According to some embodiments, the present invention provides a synergistic pharmaceutical composition comprising: artemisone, at least one compound selected from ganciclovir, BDCRB, brincidofovir, cidofovir, maribavir, valganciclovir and letermovir, and a pharmaceutically acceptable excipient, wherein the pharmaceutical composition provides a synergistic antiviral effect. The pharmaceutical composition of the present invention is useful in treating viral infection, in particular HCMV.

The term "pharmaceutical composition" as used herein refers to a compositions comprising a compound or a combination of compounds of the present invention formulated together with one or more pharmaceutically acceptable carriers.

Formulation of the pharmaceutical composition may be adjusted according to applications. In particular, the pharmaceutical composition may be formulated using a method known in the art so as to provide a rapid, continuous or delayed release of the active ingredient after administration to mammals. For example, the formulation may be any one selected from among plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, capsules, creams, troches, tinctures, pastes, pills, and soft or hard gelatin capsules. According to one embodiment, the pharmaceutical composition is formulated for oral administration. According to another embodiment, the pharmaceutical composition is formulated for IV administration. According to yet another embodiment, the pharmaceutical composition is formulated for 1M administration.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. The use of such media and agents for pharmaceutically active substances is well known in the art. The compositions may contain solid carriers or excipients such as, for example, lactose, starch or talcum or liquid carriers such as, for example, water, fatty oils or liquid paraffins.

These formulations can be produced by known methods using conventional solid carriers or excipients such as, for example, lactose, starch or talcum or liquid carriers such as, for example, water, fatty oils or liquid paraffins. Other carriers or excipients which may be used include, but are not limited to, materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates; and amino acids having from 2 to 12 carbon atoms and derivatives thereof such as, but not limited to, glycine, L-alanine, L-aspartic acid, L-glutamic acid, L-hydroxyproline, L-isoleucine, L-leucine and L-phenylalanine. Each possibility represents a separate embodiment of the present invention.

Auxiliary components such as tablet disintegrants, solubilisers, preservatives, antioxidants, surfactants, viscosity enhancers, coloring agents, flavoring agents, pH modifiers, sweeteners or taste-masking agents may also be incorporated into the composition. Suitable coloring agents include, but are not limited to, red, black and yellow iron oxides and FD & C dyes such as FD & C blue No. 2 and FD & C red No. 40 available from Ellis & Everard. Suitable flavoring agents include, but are not limited to, mint, raspberry, liquorice, orange, lemon, grapefruit, caramel, vanilla, cherry and grape flavors and any combinations thereof. Suitable pH modifiers include, but are not limited to, citric acid, tartaric acid, phosphoric acid, hydrochloric acid and maleic acid. Suitable sweeteners include, but are not limited to, aspartame, acesulfame K and thaumatin. Suitable taste-masking agents include, but are not limited to, sodium bicarbonate, ion-exchange resins; cyclodextrin inclusion compounds, adsorbates or microencapsulated actives. Each possibility represents a separate embodiment of the present invention.

In certain embodiments, a delivery vehicle is used. An exemplary delivery vehicle for the pharmaceutical compositions of the present invention is a liposome. A liposome is capable of remaining stable in a subject for a sufficient amount of time to deliver a compound of the present invention to the subject. A liposome within the scope of the present invention is preferably stable in the subject into whom it has been administered for at least about 30 minutes, more preferably for at least about 1 hour and even more preferably for at least about 24 hours.

According to other embodiment, the pharmaceutical composition may be administered via any known rout of administration. According to one embodiment, the pharmaceutical composition is administered via a route selected from the group consisting of oral, rectal, intramuscular, subcutaneous, intravenous, intraperitoneal, intranasal, intraarterial, intravesicle, intraocular, transdermal and topical. According to one embodiment, the pharmaceutical composition is orally administered. According to another embodiment, the pharmaceutical composition is administered IV. According to yet another embodiment, the pharmaceutical composition is formulated administered IM.

According to certain embodiments, the compounds and compositions of the present invention are particularly suitable for oral administration. It is contemplated that by orally administering the compounds and compositions of the present invention, a systemic effect can be achieved. In one embodiment, the compounds and compositions of the present invention are administered through nasal respiratory route. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, orally or nasally, from devices that deliver the composition in an appropriate manner.

Solutions or suspensions used for parenteral, intradermal, or subcutaneous application typically include the following components: a sterile diluent such as water for injection, saline solution, fixed oils, polyethylene glycols, glycerine, propylene glycol (or other synthetic solvents), antibacterial agents (e.g., benzyl alcohol, methyl parabens), antioxidants (e.g., ascorbic acid, sodium bisulfate), chelating agents (e.g., ethylenediaminetetraacetic acid), buffers (e.g., acetates, citrates, phosphates), and agents that adjust tonicity (e.g., sodium chloride, dextrose). The pH can be adjusted with acids or bases, such as hydrochloric acid or sodium hydroxide, for example. The parenteral preparation can be enclosed in ampules, disposable syringes or multiple dose glass or plastic vials.

Pharmaceutical compositions adapted for parenteral administration include, but are not limited to, aqueous and non-aqueous sterile injectable solutions or suspensions, which can contain antioxidants, buffers, bacteriostats and solutes that render the compositions substantially isotonic with the blood of an intended recipient. Such compositions can also comprise water, alcohols, polyols, glycerine and vegetable oils, for example. Extemporaneous injection solutions and suspensions can be prepared from sterile powders, granules and tablets.

According to one embodiment, the synergistic pharmaceutical composition comprises artemisone and ganciclovir. According to one embodiment, the molar ratio between artemisone to ganciclovir is in the range of from about 1:1000 to about 1000:1. According to another embodiment, the ratio between artemisone to ganciclovir is about 1:100 to about 100:1, about 1:50 to about 50:1, about 1:40 to about 40:1, about 1:30 to about 30:1, about 1:20 to about 20:1, about 1:10 to about 10:1, about 1:5 to about 5:1 or about 1:1. According to one embodiment, the artemisone: ganciclovir molar ratio is in the range of from 10:1 to 1:10. According another embodiment, the artemisone: ganciclovir molar ratio is in the range of from 8:1 to 1:8. According to a further embodiment, the artemisone: ganciclovir molar ratio is in the range of from 6:1 to 1:6. According to yet another embodiment, the artemisone: ganciclovir molar ratio is in the range of from 5:1 to 1:5 or from 4:1 to 1:3. According to one embodiment, the artemisone: ganciclovir molar ratio is in the range of from 3:1 to 1:3. According to another embodiment, the artemisone:ganciclovir molar ratio is in the range of from 2:1 to 1:2. According to one embodiment, the artemisone:ganciclovir molar ratio 1:1. According to some embodiments, the present invention provides a pharmaceutical composition comprising artemisone and ganciclovir, wherein said composition provides a synergistic antiviral effect and wherein the artemisone and ganciclovir has a particular defined weight ratio, e.g. about 1:50 to about 50:1, about 1:40 to about 40:1, about 1:30 to about 30:1, about 1:20 to about 20:1, about 1:10 to about 10:1, about 1:5 to about 5:1. According to some embodiments, the weight ratio is from 1:50 to 1:20, from 1:30 to 1:10 or from 1:20 to 1:2. According to one embodiment, the pharmaceutical composition is formulated for oral administration. According to another embodiment, the pharmaceutical composition is formulated for IV administration. According to one embodiment, the pharmaceutical composition comprises from 10 to 40 mg of artemisone and from 100 to 800 mg of ganciclovir.

According to another embodiment, the synergistic pharmaceutical composition comprises artemisone and maribavir. According to one embodiment, the molar ratio between artemisone to maribavir is in the range of from about 1:1000 to about 1000:1. According to another embodiment, the ratio between artemisone to maribavir is about 1:100 to about 100:1, about 1:50 to about 50:1, about 1:10 to about 10:1, about 1:5 to about 5:1 or about 1:1. According to some embodiments, the present invention provides a pharmaceutical composition comprising artemisone and maribavir, wherein said composition provides a synergistic antiviral effect and wherein the artemisone and maribavir has a particular defined weight ratio, e.g. about 1:50 to about 50:1, about 1:40 to about 40:1, about 1:30 to about 30:1, about 1:20 to about 20:1, about 1:10 to about 10:1, about 1:5 to about 5:1. According to some embodiments, the weight ratio of artemisone and maribavir is from 1:50 to 1:20, from 1:30 to 1:10 or from 1:20 to 1:2. According to one embodiment, the pharmaceutical composition is formulated for oral administration. According to another embodiment, the pharmaceutical composition is formulated for IV administration. According to one embodiment, the oral pharmaceutical composition comprises from 10 to 40 mg of artemisone and from 100 to 480 mg of maribavir.

According to one embodiment, the synergistic pharmaceutical composition comprises artemisone and BDCRB. According to one embodiment, the molar ratio between artemisone to BDCRB is in the range of from about 1:1000 to about 2000:1. According to another embodiment, the ratio between artemisone to BDCRB is about 1:100 to about 200:1, about 1:50 to about 100:1, about 1:10 to 20:1, 1:5 to 10:1 or 2:1. According to one embodiment, the pharmaceutical composition is formulated for oral administration. According to another embodiment, the pharmaceutical composition is formulated for IV administration.

According to one embodiment, the synergistic pharmaceutical composition comprises artemisone and letermovir. According to one embodiment, the molar ratio between artemisone and letermovir is in the range of from 1:5 to 200000:1. According to another embodiment, the ratio between artemisone and letermovir is in the range of from 2:1 to 20000, 4:1 to 10000:1, 20:1 to 2000:1 or 100:1 to 250:1, or 200:1. According to some embodiments, the present invention provides a pharmaceutical composition comprising artemisone and letermovir, wherein said combination provides a synergistic antiviral effect and wherein the artemisone and letermovir has a particular defined weight ratio, e.g. about 1:50 to about 50:1, about 1:40 to about 40:1, about 1:30 to about 30:1, about 1:20 to about 20:1, about 1:10 to about 10:1, about 1:5 to about 5:1. According to some embodiments, the weight ratio of artemisone and letermovir is from 1:50 to 1:20, from 1:30 to 1:10 or from 1:20 to 1:3. According to one embodiment, the pharmaceutical composition is formulated for oral administration. According to another embodiment, the pharmaceutical composition is formulated for IV administration.

According to one embodiment, the synergistic pharmaceutical composition comprises artemisone and brincidofovir. According to one embodiment, the molar ratio between artemisone and brincidofovir is in the range of from 1:1 to $10^6$:1. According to another embodiment, the ratio between artemisone and brincidofovir is in the range of from 10:1 to $10^5$:1, 100:1 to $10^4$:1, 500:1 to 1500:1, or 1000:1. According to one embodiment, the pharmaceutical composition is formulated for oral administration. According to another embodiment, the pharmaceutical composition is formulated for IV administration.

According to one embodiment, the synergistic pharmaceutical composition comprises artemisone and cidofovir. According to another embodiment, the ratio between artemisone and cidofovir is in the range of from 2500:1 to 1:400, or from 250:1 to 1:40 or from 25:1 to 1:4. According to one embodiment, the pharmaceutical composition is formulated for oral administration. According to another embodiment, the pharmaceutical composition is formulated for IV administration. According to yet another embodiment, the pharmaceutical composition is formulated for IM administration.

According to one embodiment, the synergistic pharmaceutical composition comprises artemisone and valganciclovir. According to one embodiment, the molar ratio between artemisone to valganciclovir is in the range of from about 1:1000 to about 1000:1. According to another embodiment, the ratio between artemisone to ganciclovir is about 1:100 to about 100:1, about 1:50 to about 50:1, about 1:10 to about 10:1, about 1:5 to about 5:1 or about 1:1. According to one embodiment, the pharmaceutical composition is formulated for oral administration. According to another embodiment, the pharmaceutical composition is formulated for IV administration. According to one embodiment, the pharmaceutical composition comprises from 10 to 40 mg of artemisone and from 100 to 800 mg of valganciclovir. According to one embodiment, the pharmaceutical composition is formulated for oral administration. According to another embodiment, the pharmaceutical composition is formulated for IV administration. According to yet another embodiment, the pharmaceutical composition is formulated for IM administration.

According to some embodiments, the present invention provides a pharmaceutical composition comprising artemisone and at least one compound selected from ganciclovir, BDCRB, brincidofovir, cidofovir, valganciclovir, maribavir and letermovir, wherein the amount of artemisone and said at least one compound is such that the $EC_{50}$ ratio of artemisone and said compound is in the range of from 20:1 to 1:20, from 15:1 to 1:15 or from 10:1 to 1:10. According to one embodiment, the $EC_{50}$ ratio is in the range of 12:1 to 1:12, 8:1 to 1:8 or 5:1 to 1:5. According to one embodiment, the $EC_{50}$ ratio is in the range of from 3:1 to 1:3

According to any one of the above embodiments, the terms "artemisone", "ganciclovir", "BDCRB", "brincidofovir", "cidofovir", "maribavir", "valganciclovir" and "letermovir" encompasses also the pharmaceutically acceptable salts and isomers thereof.

According to any one of the above embodiments, the pharmaceutical composition formulated for oral administration is in a form of tablets, capsules or powder. According to other embodiment, the pharmaceutical composition formulated for parenteral administration such as intravenous (IV) or intramuscular (IM) administration are in the form of sterile solution or suspension.

According to some embodiments, the synergistic pharmaceutical composition of the present invention has a synergistic antiviral effect characterized by a weighted average Combination Index (CIwt) value between 0.1 to 0.9, between 0.2 to 0.85, between 0.25 to 0.8, between 0.3 to 0.75, between 0.4 to 0.7, between 0.45 to 0.65 or between 0.5 to 0.6. According to another embodiment, the synergistic antiviral effect is characterized by a CIwt value between 0.2 to 0.5, or between 0.25 to 0.4.

According to some embodiments, the synergistic pharmaceutical composition comprises artemisone and at least one compound selected from ganciclovir, BDCRB, brincidofovir, cidofovir, maribavir, valganciclovir and letermovir, wherein the amount of artemisone is at least 1.5 times lower than in the standard corresponding dose of artemisone. According to other embodiment, the synergistic pharmaceutical composition comprises artemisone and at least one compound selected from ganciclovir, BDCRB, brincidofovir, cidofovir, maribavir, valganciclovir and letermovir, wherein the amount of said at least one compound is at least 1.5 times lower than in the standard corresponding dose of said compound. According to yet another embodiment, the amount of artemisone and of said at least one compound is at least 1.5 times lower than the standard corresponding dose of artemisone and of said compound. According to another embodiment, the amount of said at least one compound in the synergistic pharmaceutical composition of the present invention is at least 2, at least 3, at least 4, at least 5, at least 6 at least 8, at least 10, at least 20 or at least 50 times lower than in the standard correspondent dose of said compound, and/or the amount of artemisone is at least 2, at least 3, at least 4, at least 5, at least 6 at least 8, at least 10, at least 20 or at least 50 times lower than in the standard correspondent antiviral dose. According to one embodiment, the synergistic pharmaceutical composition comprises artemisone and at least one compound selected from ganciclovir, BDCRB, brincidofovir, cidofovir, maribavir, valganciclovir and letermovir, wherein the amount of artemisone and/or said at least one compound is at least 2 times lower than the amount required for obtaining the same level of antiviral affect if artemisone or said at least one compound is administered alone. According to another embodiment, the amount of said at least one compound in the synergistic pharmaceutical composition of the present invention is at least 3, at least 4, at least 5, at least 6 at least 8, at least 10, at least 20 or at least 50 times lower than the amount required for obtaining the same antiviral affect if said at least one compound is administered alone, and/or the amount of artemisone in said composition is at least 3, at least 4, at least 5, at least 6 at least 8, at least 10, at least 20 or at least 50 times lower than the amount required for obtaining the same antiviral affect if artemisone is administered alone. The terms "correspondent dose" and "corresponding dose" are used herein interchangeably and have the meaning of a dosage form formulated and administered in the same route of administration as the dosage form referring to it.

According to another embodiment, the amount of artemisone is from 2 to 50 folds lower than the amount required for obtaining the same antiviral affect when artemisone is administered alone. According to certain embodiments, the amount of at least one compound selected from ganciclovir, BDCRB, brincidofovir, cidofovir, maribavir, valganciclovir and letermovir, is from 2 to 35 folds lower than the amount required for obtaining the same antiviral affect when said at least one compound is administered alone. According to yet another embodiment, the amount of arteminone and at least one compound selected from ganciclovir, BDCRB, brincidofovir, cidofovir, maribavir and letermovir, is from 2 to 35 folds lower than the amount required for obtaining the same antiviral affect when artemisine or said at least one compound, respectively, is administered alone. According one embodiment, the amount of artemisone and at least one compound selected from ganciclovir, BDCRB, brincidofovir, cidofovir, maribavir, valganciclovir and letermovir, is 2, 3, 4, 5, 6, 7, 8, 9 or 10 times lower than the amount required for obtaining the same antiviral affect when artemisone or said at least one compound, respectively, is administered alone. According to one embodiment, the amount of artemisone the is from 3 to 19 folds lower and the amount of brincidofovir of from 1.3 to 1.7 or from 1.4 to 1.6, or from 1.43 to 1.54 folds lower than the amount of these drugs required for obtaining the same antiviral affect when administered alone.

According to some embodiments, the pharmaceutical composition for oral administration comprises from 1 to 400 mg of artemisone. According to some embodiments, the daily oral dose of artemisone is in the range of from 2 to 350, 5 to 320, 8 to 300, 10 to 280, 20 to 240, 35 to 210, 40 to 200, 45 to 180, 50 to 160, 55 to 140, 60 to 120, 80 to 100 mg/day. According to other embodiments, the oral pharmaceutical composition comprises from 2 to 350, 5 to 320, 8 to 300, 10 to 280, 20 to 240, 35 to 210, 40 to 200, 45 to 180, 50 to 160, 55 to 140, 60 to 120, 80 to 100 mg of artemisone. According to some embodiment, artemisone is orally administered in a single dose or in several separate doses. Thus, according to some embodiments, artemisone is orally administered in a dose of 10, 20, 30, 40, 50, 60 or 80 mg 2, 3, 4, 5 or 6 times a day. According to one embodiment, artemisone is administered in a dose regimen of 10, 20, 40, 60 or 80 mg/TID. According to another embodiment, artemisone is intravenously administered in the dose of from 1 to 3 mg/kg. According to some embodiments, artemisone is systemically administered in a dose providing the antiviral effect obtained by a single IV administering of 1 to 3 mg/kg. According to some embodiments, the pharmaceutical composition comprises 10, 20, 30, 40, 50, 60 or 80 mg of artemisone.

According to some embodiments, the pharmaceutical composition comprises an amount of artemisone providing the AUC corresponding the AUC obtained upon single administration of from 1 to 3 mg/kg artemisone intravenously (IV). Corrections related to oral bioavailability of drugs vs IV availability may be required.

According to such embodiments, the dose of ganciclovir, BDCRB, brincidofovir, cidofovir, maribavir, valganciclovir and letermovir in the pharmaceutical composition is defined by the dose of artemisone and the molar ratio as defined in the present invention.

According to another embodiment, the dose of artemisone and at least one antiviral compound selected from ganciclovir, BDCRB, brincidofovir, cidofovir, maribavir, valganciclovir and letermovir is defined by the DRIs of these compound for a given synergic composition, as described herein above.

According to some embodiments, the synergistic pharmaceutical composition of the present invention is for use in treating a viral infection or in suppressing viral replication, wherein administering said composition provides a synergistic antiviral effect. According to one embodiment, the composition is for use in suppressing or inhibiting viral infection, suppressing or inhibiting viral replication, prevention and/or prophylaxis of the viral infection, preventing maternal fetal transmission, and reducing inhibiting, preventing /or treating congenital infection or preventing viral spread. According to one embodiment, the viral infection or replication is herpesvirus infection or replication, as defined in any one of the above aspects and embodiments. According to certain embodiments, the herpesvirus is CMV such as HCMV. Thus, in one embodiment, the present invention provides a synergic pharmaceutical composition comprising artemisone and at least one antiviral compound selected from ganciclovir, BDCRB, brincidofovir, cidofovir, maribavir, valganciclovir and letermovir, for use in treating HCMV, wherein said use provides a synergic antiviral effect.

According to another aspect, the present invention provides a combination of artemisone and at least one compound selected from the group consisting of BDCRB, brincidofovir, cidofovir, maribavir, valganciclovir and letermovir for preparation of a medicament for treatment of a viral infection or disease. According to one embodiment, the present invention provides use of artemisone and ganciclovir for preparation of a medicament for treating a viral infection or disease.

According to another aspect, the present invention provides a method of treating a viral infection or of suppressing viral replication in a subject in need thereof comprising co-administering artemisone and at least one compound selected from the group consisting of BDCRB, brincidofovir, cidofovir, maribavir, valganciclovir and letermovir, wherein said co-administering provides a synergistic antiviral effect. According to one embodiment, the co-administering is performed in a sequential manner or in a substantially simultaneous manner. According to some embodiments, treating comprises suppressing or inhibiting viral infection. According to other embodiments, treating comprises suppressing or inhibiting viral replication. According to other embodiments, treating comprises prevention and/or prophylaxis of the viral infection. According to some embodiments, treating comprises preventing maternal fetal transmission. According to certain embodiments, treating comprises preventing and/or treating congenital infection. According to some embodiments, treating comprises reducing inhibiting or preventing viral spread.

The terms "co-administration" as used herein have the meaning of administering two or more compounds in a regimen selected from a single combined composition, separate individual compositions administered substantially at the same time, and separate individual compositions administered under separate schedules and include treatment regimens in which the compounds are not necessarily administered by the same route of administration or at the same time. According to some embodiments, the term "co-administration" encompasses administration of a first and second compound in an essentially simultaneous manner, such as in a single dosage form, e.g., a capsule or tablet having a fixed ratio of first and second amounts, or in multiple dosage forms for each. The agents can be administered in a sequential manner in either order. According to some embodiment, each antiviral compound is administered in an individual dosage form and in an administration regimens which are may be different from and non-related to each other. According to some embodiments, the viral infection or replication is an HCMV infection or replication. According to one embodiment, the present invention provides a method of treating a viral infection or of suppressing viral replication in a subject in need thereof comprising co-administering artemisone and ganciclovir in a particular weight/molar ratio, e.g. about 1:1000 to about 1000:1, about 1:100 to about 100:1, about 1:50 to about 50:1, about 1:10 to about 10:1, about 1:5 to about 5:1 or about 1:1.

According to some embodiments, the daily oral dose of artemisone is in the range of from 2 to 350, 5 to 320, 8 to 300, 10 to 280, 20 to 240, 35 to 210, 40 to 200, 45 to 180, 50 to 160, 55 to 140, 60 to 120, 80 to 100 mg/day. According to some embodiment, artemisone is administered in a single dose or in several separate doses. Thus, according to some embodiments, artemisone is orally administered in a dose of 10, 20, 30, 40, 50, 60 or 80 mg 2, 3, 4, 5 or 6 times a day. According to one embodiment, artemisone is orally administered in a dose regiment of 10, 20, 40, 60 or 80 mg/TID. According to another embodiment, artemisone is intravenously administered in the dose of from 1 to 3 mg/kg. According to some embodiments, artemisone is systemically administered in a dose providing the antiviral effect obtained by IV administering of 1 to 3 mg/kg.

According to some embodiments, the daily oral dose provides the AUC corresponding the AUC obtained upon single administration of from 1 to 3 mg/kg artemisone intravenously (IV).

According to such embodiments, the dose of ganciclovir, BDCRB, brincidofovir, cidofovir, maribavir, valganciclovir and letermovir is defined by the dose of artemisone and the molar, weight and/or $EC_{50}$ ratio defined in the present invention.

According to another embodiment, the dose of artemisone and at least one antiviral compound selected from ganciclovir, BDCRB, brincidofovir, cidofovir, maribavir, valganciclovir and letermovir is determined according to the DRIs of these compounds in the synergic combination considering the desired antiviral effect.

According to one embodiment, for a combination of artemisone and ganciclovir, the DRI of artemisone is from about 7 to about 16 and the DRI of ganciclovir is from about 1.97 to about 2.2 for affecting 90-97% of viruses. According to another embodiment, for a combination of artemisone and maribavir, the DRI of artemisone is from about 28.7 to about 40.8 and the DRI of maribavir is from about 12.98 to about 20.6 for affecting 90-97% of viruses. According to another embodiment, for a combination of artemisone and maribavir, the DRI of artemisone is from about 5.8 to about 15 and the DRI of maribavir is from about 1.3 to about 1.5 for affecting 90-97% of viruses. According to another embodiment, for a combination of artemisone and letermovir, the DRI of artemisone is from about 7 to about 16.5 and the DRI of letermovir is from about 1.7 to about 2.36 for affecting 90-97% of viruses. According to a further embodiment, for a combination of artemisone and cidofovir, the DRI of artemisone is from about 8 to about 17 and the DRI of cidofovir is from about 2.6 to about 3.2 for affecting 90-97% of viruses. According to another embodiment, for a combination of artemisone and brincidofovir, the DRI of artemisone is from about 12.7 to about 20 or from about 10 to about 19 or from about 12.7 to about 18.7 and the DRI of brincidofovir is from about 1.3 to about 1.6 or from 1.45 to about 1.54 for affecting 90-97% of viruses.

The administration schedule can be administering once-daily, twice-daily, thrice-daily, once-weekly, twice-weekly, thrice-weekly, once-monthly, twice-monthly, thrice-monthly, or any other administration schedule known to those of skill in the art. In addition, the administration can be continuous, i.e., every day, or intermittently. The terms "intermittent" or "intermittently" as used herein means stopping and starting at either regular or irregular intervals. For example, intermittent administration can be administration in one to six days per week or it may mean administration in cycles (e.g. daily administration for two to eight consecutive weeks, then a rest period with no administration for up to one week) or it may mean administration on alternate days.

According to another aspect, the present invention provides a kit comprising a pharmaceutical composition comprising artemisone, a pharmaceutical composition comprising at least one compound selected from the group consisting of brincidofovir, cidofovir, maribavir, valganciclovir and letermovir, and instructions for use of said compositions. According to some embodiments, the doses of artemisone, ganciclovir, BDCRB, brincidofovir, cidofovir, maribavir, valganciclovir and letermovir, the molar, weight and $EC_{50}$ ratios are as defined in any one of the above aspects and embodiments According to one embodiment, the present invention provides a kit comprising a pharmaceutical composition comprising artemisone, a pharmaceutical composition comprising ganciclovir, and instructions for use of said compositions, wherein the ratio between artemisone and ganciclovir is in the range of from 1:100 to 100:1. According to one embodiment, the kit is for use in treating viral infection or disease.

The following examples are presented in order to more fully illustrate some embodiments of the invention. They should, in no way be construed, however, as limiting the broad scope of the invention.

EXAMPLES

Example 1

Synergistic Antiviral Effect of a Combination of Artemisone with Several Antiviral Drugs Materials and Methods
Virus, Cells, and Tested Compounds
The CMV strain used was TB40/E. The CMV strain was propagated and tittered in human foreskin fibroblasts (HFF) cells. Cell-free virus stocks and cell-associated clinical isolates were maintained at −70° C. Viral stocks were tittered by serial 10-fold dilution in 24-well tissue culture plates containing HFF monolayers overlaid with agarose-medium. After incubation for 7 to 14 days, plaques were enumerated, and virus titer was determined as plaque forming units (PFU) per milliliter (ml). Stocks of artemisone (10 mM), ganciclovir (10 mM), BDCRB (120 mM), brincidofovir (1 mM), maribavir (10 mM) and letermovir (10 mM) were prepared in DMSO or H2O.

Plaque Reduction Assay
Cell monolayers were inoculated in 24-well culture plates with 0.2 ml of virus suspension containing 60 to 100 PFU per well. After adsorption for 60 -120 min at 37° C., the inoculum was removed, and culture medium was replaced with agarose-medium overlay containing serial concentrations of the tested drug(s). Plates were incubated for 7-14 days at 37° C. in a 5% CO2 incubator. Plaques were then counted microscopically.

Results
The effect of a combination of artemisone with each one of ganciclovir (HCMV DNA polymerase), BDCRB (HCMV terminase inhibitor), brincidofovir (HCMV DNA polymerase inhibitor), maribavir (HCMV UL97 kinase inhibitor) and letermovir (HCMV terminase inhibitor) was evaluated by the classical plaque reduction assay. The in vitro activity of each of the above mentioned antiviral compounds alone or in combination with artemisone was evaluated by the classical plaque reduction assay, using HCMV TB40/E strain in human foreskin fibroblasts cells. The concentration of each antiviral compound that reduced the plaque formation by 50% ($EC_{50}$) was determined as previously described in Wolf DG et al., J Clin Invest. 1995;95:257-63. The individual $EC_{50}$ values in human foreskin fibroblasts were as follows: artemisone $EC_{50}$-1 µM; ganciclovir $EC_{50}$-1 µM; maribavir $EC_{50}$-1 µM; BDCRB $EC_{50}$-0.5 µM; letermovir $EC_{50}$-5 nM; brincidofovir $EC_{50}$-1 nM.

To determine whether the combination results in a synergistic, additive, or antagonistic effect on HCMV replication a Chou-Talalay method was implemented (Chou T C. Pharmacol Rev 2006; 58: 621-81).

For the 2-drug combination studies, the $EC_{50}$ value of each drug was used to determine an equipotent ratio between the two compounds ($EC_{50}$ of drug 1/$EC_{50}$ of drug 2). Serial 2-fold dilutions of a mixture comprising artemisone and another antiviral compound at initial concentrations equivalent to 4-fold the equipotent ratio were added to duplicate wells of cells infected with HCMV. Overall, 5 different concentrations of the drug combinations were used: $4 \times EC_{50}$, $2 \times EC_{50}$, $1 \times EC_{50}$, $0.5 \times EC_{50}$, $0.25 \times EC_{50}$. The cell monolayers were inoculated in 24-well culture plates with 0.2 ml of virus suspension containing 60 to 100 plaque-forming unit (PFU) per well; the Multiplicity of infection (MOI) was 0.001-0.002 PFU/cell).

The combination index (CI) method of Chou-Talalay method provides quantitative determination for synergism, additive effect and antagonism, and provides the algorithm for computer software for automated simulation for drug combinations.

CI is defined as $$CI = \frac{(D)_1}{(D_x)_1} + \frac{(D)_2}{(D_x)_2} = \frac{1}{(DRI)_1} + \frac{1}{(DRI)_2}$$

$D_1$ and $D_2$ are the doses of the two drugs, and Dx is a dose causing to x % effect (LD0.5 is $EC_{50}$). Briefly, the software extrapolated a combination index (CI) representing the interaction between the two drugs at specified levels of virus inhibition (that is 50%, 75%, 90%, 95%) versus the percentages of the inhibition induced by each drug alone and in combination (equation 16 in Chou).

A weighted average CI ($CI_{wt}$) was then calculated for each combination as $(CI_{50}+2\times CI_{75}+3\times CI_{90}+4\times CI95)/10$, to access the drug combinatory effects. Drug combinatory effects, computed in the CalcuSyn software version 1.0 (Biosoft, Cambridge, UK), were defined as: strong synergism for $CI_{wt}$ 0.1-0.3, synergism for $CI_{wt}$ 0.3-0.7, moderate synergism for $CI_{wt}$ 0.7-0.9, addition for $CI_{wt}$ 0.9-1.2, moderate antagonism for $CI_{wt}$ 1.2-1.45, and antagonism for $CI_{wt>}$1.45. The results are presented in Table 1.

TABLE 1

The synergistic antiviral effect of artemisone in combination with one of 6 antiviral compounds.

| Drug combination (molar ratio at equipotent concentration) | CI values extrapolated at % of virus inhibition | | | | $CI_{wt}$ | Drug combinatory effect |
|---|---|---|---|---|---|---|
| | 50 | 75 | 90 | 95 | | |
| artemisone + ganciclovir (1:1) | 1.22 ± 0.47 | 0.89 ± 0.25 | 0.68 ± 0.09 | 0.58 ± 0.04 | 0.73 ± 0.14 | Moderate synergism |
| artemisone + maribavir (1:1) | 0.48 ± 0.26 | 0.31 ± 0.17 | 0.21 ± 0.11 | 0.16 ± 0.08 | 0.27 ± 0.08 | Strong synergism |
| artemisone + BDCRB (2:1) | 1.15 ± 0.12 | 0.93 ± 0.11 | 0.81 ± 0.14 | 0.75 ± 0.16 | 0.84 ± 0.12 | Moderate synergism |
| artemisone + letermovir (200:1) | 1.20 ± 0.34 | 0.91 ± 0.12 | 0.76 ± 0.04 | 0.70 ± 0.12 | 0.81 ± 0.01 | Moderate synergism |
| artemisone + brincidofovir (1000:1) | 0.88 ± 0.31 | 0.50 ± 0.17 | 0.34 ± 0.26 | 0.27 ± 0.29 | 0.39 ± 0.22 | Synergism |
| artemisone + cidofovir (2.5:1) | 0.95 ± 0.16 | 0.71 ± 0.07 | 0.55 ± 0.05 | 0.47 ± 0.05 | 0.6 ± 0.05 | Synergism |
| ganciclovir + maribavir (1:1) | 2.11 ± 0.84 | 2.50 ± 0.42 | 3.77 ± 2.21 | 5.53 ± 4.15 | 4.02 ± 2.30 | Antagonism |

It can be clearly seen from these results that the combination of artemisone with (i) ganciclovir, (ii) BDCRB, or (iii) letermovir, resulted in moderate synergism. The combination of artemisone with maribavir demonstrated strong synergistic effect, and the combination of artemisone with brincidofovir or with cidofovir both demonstrated synergistic effect. As expected, the combination of maribavir with ganciclovir resulted in an antagonistic effect, in accordance with their interfering mechanism of action—supporting the validity of the analysis.

The dose reduction index (DRI) was then calculated as described in Chou. The results are presented in Tables 2-6. In general, the DRI measures the fold of dose reduction of each drug in the combination at a given effect level compared with the doses of each drug alone. For each one of the below tables: Fa—fraction of virus affected; doses are provided in p.m.

TABLE 2

DRI for drug combination of artemisone (Art) + ganciclovir (GCV)

| Fa | Dose Art | Dose GCV | DRI Art | DRI GCV |
|---|---|---|---|---|
| 0.05 | 0.02184 | 0.10386 | 0.28216 | 1.34206 |
| 0.5 | 0.62597 | 0.58432 | 1.79250 | 1.67321 |
| 0.75 | 2.18940 | 1.11316 | 3.57317 | 1.81672 |
| 0.9 | 7.65765 | 2.12066 | 7.12278 | 1.97253 |
| 0.95 | 17.9447 | 3.28739 | 11.3872 | 2.08608 |
| 0.97 | 32.8918 | 4.49067 | 15.9002 | 2.17083 |

TABLE 3

DRI for drug combination of artemisone (Art) + maribavir (MBV)

| Fa | Dose Art | Dose MBV | DRI Art | DRI MBV |
|---|---|---|---|---|
| 0.05 | 0.02184 | 0.00633 | 7.03234 | 2.03874 |
| 0.5 | 0.62597 | 0.23392 | 15.7458 | 5.88404 |

TABLE 3-continued

DRI for drug combination of artemisone (Art) + maribavir (MBV)

| Fa | Dose Art | Dose MBV | DRI Art | DRI MBV |
|---|---|---|---|---|
| 0.75 | 2.18940 | 0.89944 | 21.2706 | 8.73828 |
| 0.9 | 7.65765 | 3.45842 | 28.7339 | 12.9771 |
| 0.95 | 17.9447 | 8.64366 | 35.2558 | 16.9821 |
| 0.97 | 32.8918 | 16.5865 | 40.7793 | 20.5640 |

TABLE 4

DRI for drug combination of artemisone (Art) + letermovir (Let)

| Fa | Dose Art | Dose Let | DRI Art | DRI Let |
|---|---|---|---|---|
| 0.05 | 0.02184 | 2.51E-4 | 0.22755 | 0.52256 |
| 0.5 | 0.62597 | 0.00201 | 1.62373 | 1.04365 |
| 0.75 | 2.18940 | 0.00438 | 3.38022 | 1.35097 |
| 0.9 | 7.65765 | 0.00952 | 7.03682 | 1.74878 |
| 0.95 | 17.9447 | 0.01614 | 11.5866 | 2.08436 |
| 0.97 | 32.8918 | 0.02351 | 16.5217 | 2.36167 |

TABLE 5

DRI for drug combination of artemisone (Art) + brincidofovir (BCV)

| Fa | Dose Art | Dose BCV | DRI Art | DRI BCV |
|---|---|---|---|---|
| 0.05 | 0.02 | 1.87E-4 | 0.16 | 1.43 |
| 0.5 | 0.63 | 6.49E-4 | 1.44 | 1.48 |
| 0.75 | 2.23 | 0.001 | 3.24 | 1.5 |

TABLE 5-continued

DRI for drug combination of artemisone (Art) + brincidofovir (BCV)

| Fa | Dose Art | Dose BCV | DRI Art | DRI BCV |
|---|---|---|---|---|
| 0.9 | 7.87 | 0.002 | 7.28 | 1.52 |
| 0.95 | 18.59 | 0.002 | 12.65 | 1.53 |
| 0.97 | 34.26 | 0.003 | 18.74 | 1.54 |

TABLE 6

DRI for drug combination of artemisone (Art) + cidofovir (CDV)

| Fa | Dose Art | Dose CDV | DRI Art | DRI CDV |
|---|---|---|---|---|
| 0.05 | 0.06103 | 0.07783 | 0.32558 | 1.03807 |
| 0.5 | 1.05887 | 0.36350 | 2.04749 | 1.75722 |
| 0.75 | 3.07079 | 0.64603 | 4.06609 | 2.13855 |
| 0.9 | 8.90550 | 1.14815 | 8.07482 | 2.60263 |
| 0.95 | 18.3723 | 1.69770 | 12.8761 | 2.97457 |
| 0.97 | 30.7567 | 2.24245 | 17.9464 | 3.27116 |

As can be seen from Table 2, the concentration of artemisone required for affecting 90% of the viruses is 7.66 μm and for ganciclovir the concentration is 2.12 μm. The same effect may be obtained by the combination of artemisone and ganciclovir in which the concentration of these compounds is significantly reduced. In order to provide the same effect, i.e. affecting 90% of the viruses, the required concentration of artemisone and ganciclovir were 7.12 and 1.97 times lower, respectively, than the concentrations required when these drugs were administered alone. Considering affecting 95% of the viruses, it can be seen from Table 2 that the DRI of artemisone and of ganciclovir were 11.39 and 2.09 respectively, meaning that the concentrations of these drugs may be reduced 11.39 and 2.09 folds, respectively, in comparison to their concentration when the drugs were administered alone. Usually, in clinic affecting 90-99% of viruses is desired. Thus, the concentration of each one of these drugs may be reduced. The concentration of artemisone was reduced about 7 folds and the concentration of ganciclovir was reduced about 2 folds and still the desired clinical effect was obtained.

By combining artemisone and maribavir it is possible to reduce the concentration of these drugs 28.7 and 12.98 times, respectively, in comparison to concentrations of these drugs required to affect 90% of viruses when each of the drugs is administered alone. For affecting 97% of viruses, the DRIs for artemisone and maribavir were 40.8 and 20.6, respectively.

Similarly, the DRIs of artemisone and letermovir administered as a combination were 7.04 and 1.75, respectively, for affecting 90% of the viruses. The concentration of artemisone may be reduced up to 16 folds and the concentration of letermovir up to 2.4 folds in comparison to concentration when said drugs are administered as a sole treatments, if affecting 97% of viruses is required.

A profound effect was observed for the combination of artemisone and brincidofovir. The concentration of artemisone may be reduced up to 7 fold and the concentration of brincidofovir up to 1.5 folds in comparison to the concentrations of these drugs if administered as a single therapy for affecting 90% of viruses.

The DRIs of artemisone and cidofovir, administered as a combination, were 8.07 and 2.6, respectively for affecting 90% of the viruses. The concentration of artemisone may be reduced up to 17.9 folds and of cidofovir up to 3.27 folds if affecting 97% of viruses is required.

Example 2

Testing the Synergistic Effect of Artemisone and Antiviral Compounds Ex Vivo in Human Placental Tissues Materials and Methods
RNA Quantification Organ cultures were washed and stored at −80° C. until assayed. RNA was extracted, and the purified RNA samples were subjected to reverse transcription (RT), followed by quantitative real-time PCR. The viral mRNA copy number was normalized by the cellular housekeeping gene β-actin.

Determination of $EC_{50}$ in Ex Vivo Model

The synergic effect of artemisone and maribavir was tested in a clinically-relevant ex vivo model of the human placenta. We employed our model of HCMV infection in human decidual tissues (representing the maternal aspect of the chimeric human placenta), maintained as multi-cell-type 3D organ cultures as described in Weisblum Y. et al. J Virol 2011 85(24): 13204-13. doi: 10.1128/JVI.05749-11. For infection of the organ cultures, decidual tissues were placed in 48-well plates and inoculated with the virus ($5 \times 10^4$ plaque forming units (PFU)/well) for 12 h to allow effective viral adsorption. The tissues were further monitored for viral infection and spread for 7 days. For determination of the drug $EC_{50}$ values of in the tissues, serial drug concentrations: each drug separately or combination of the drugs were added to the infected decidual tissues during viral adsorption at any further medium replacement to keep the drug concentration constant. The results were compared to samples to which the drug was not added. The $EC_{50}$ was defined as the drug concentration required to reduce the viral mRNA copy number by 50%. The effect of drug combinations was tested in accordance with the Chou-Talalay method. All comparative experiments were performed in parallel on tissues from the same donor.

Results

The $EC_{50}$ of artemisone and maribavir, used as a sole drug in ex-vivo model was 0.5 μM and 0.25 μM, respectively. The combination of artemisone with maribavir demonstrated a synergistic antiviral (anti-HCMV) effect ex vivo, in a clinically-relevant multicellular model of integral human placental (decidual) tissues maintained in organ culture. The calculated CIwt (see Table 7) clearly shows that combination of artemisone and maribavir have a synergistic antiviral effect.

TABLE 7

The synergistic antiviral effect of artemisone and Marivabir ex vivo

| Drug combination (molar ratio at equipotent concentration) | CI values extrapolated at % of virus inhibition | | | | Drug combinatory effect |
|---|---|---|---|---|---|
| | 50 | 75 | 90 | 95 | $CI_{wt}$ | |
| artemisone + maribavir (2:1) | 1.33 ± 0.79 | 0.74 ± 0.16 | 0.48 ± 0.14 | 0.38 ± 0.2 | 0.56 ± 0.08 | Synergism |

The dose reduction index (DRI) was then calculated as described in Chou. The results are presented in Tables 8. As described earlier, the DRI is a measure of how many folds the dose of each drug in a synergistic combination may be reduced at a given effect level compared with the doses of each drug alone. For each one of the below tables: Fa—fraction of virus affected; doses are provided in μm.

TABLE 8

DRI for drug combination of artemisone
(Art) + maribavir (MBV) ex vivo

| Fa | Dose Art | Dose MBV | DRI Art | DM MBV |
|---|---|---|---|---|
| 0.05 | 0.00699 | 0.01861 | 0.12387 | 0.65995 |
| 0.5 | 0.42458 | 0.18618 | 1.11969 | 0.98198 |
| 0.75 | 1.96536 | 0.43961 | 2.54591 | 1.13893 |
| 0.9 | 9.09767 | 1.03802 | 5.78878 | 1.32097 |
| 0.95 | 25.7963 | 1.86206 | 10.1210 | 1.46114 |
| 0.97 | 54.1517 | 2.82209 | 15.0614 | 1.56984 |

As can be seen from Table 8, the concentration of artemisone required for affecting 90% of the viruses is 9.1 μm and for maribavir the concentration is 1.03 μm. The same effect may be obtained by the combination of artemisone and maribavir in which the concentration of these compounds is significantly reduced. In order to provide the same effect, i.e. affecting 90% of the viruses, the required concentration of artemisone in combination with maribavir in the combination were 5.8 and 1.3 times lower, respectively, than the concentrations required if these drugs were administered alone. Considering affecting 95% of the viruses, it can be seen from Table 8 that the DRI of artemisone and of maribavir were 10.1 and 1.46 respectively. Usually, in clinic affecting 90-99% of viruses is desired. Thus the concentration of each one of these drugs may be reduced. The concentration of artemisone in the combination of artemisone and maribavir may be reduced up to 10 folds and the concentration of maribavir in the combination may be reduced up to 1.5 folds and still the desired clinical effect is obtained.

Although the present invention has been described herein above by way of preferred embodiments thereof, it can be modified, without departing from the spirit and nature of the subject invention as defined in the appended claims.

The invention claimed is:

1. A method of treating a viral infection in a subject in need thereof comprising co- administering to said subject artemisone and maribavir, wherein said co-administering provides a synergistic antiviral effect.

2. The method of claim 1, wherein the molar ratio of artemisone to maribavir is in the range of from 1:100 to 100:1 or from 1:10 to 10:1.

3. The method of claim 1, wherein said co-administering is performed in a regimen selected from a sequential manner or a substantially simultaneous manner.

4. The method of claim 1, wherein the daily administered dose of artemisone and/or of maribavir is lower than the standard daily dose of artemisone and/or of maribavir.

5. The method of claim 1, wherein artemisone and maribavir, are formulated in a single dosage form.

6. The method of claim 5, wherein the single dosage form is a pharmaceutical composition comprising said compounds and a pharmaceutically acceptable carriers and/or excipients.

7. The method of claim 1, wherein said viral infection is a herpesvirus infection.

8. The method of claim 7, wherein the herpesvirus is a human cytomegalovirus (HCMV).

9. The method of claim 1, wherein the treating comprises suppressing or inhibiting viral infection; suppressing or inhibiting viral replication; prevention and/or prophylaxis of the viral infection;
    preventing maternal fetal transmission; preventing/or treating congenital infection; and reducing, inhibiting, or preventing viral spread.

10. The method of claim 1, wherein the subject is selected from the group consisting of a newborn, a pregnant woman and a transplant recipient.

11. A synergistic pharmaceutical composition comprising artemisone, maribavir, and a pharmaceutically acceptable excipient or carrier, wherein the pharmaceutical composition provides a synergistic antiviral effect.

12. The synergistic pharmaceutical composition of claim 11, wherein the molar ratio of artemisone and maribavir is in the range of from 1:100 to 100:1 or from 1:10 to 10:1.

13. The synergistic pharmaceutical composition of claim 11, wherein the amount of maribavir is lower than the amount of maribavir in a standard corresponding dosage form and/or the amount of artemisone is lower than the amount in a standard corresponding dosage form of artemisone.

14. A method for treating a viral infection in a subject in need thereof comprising administering to said subject a synergistic pharmaceutical composition comprising artemisone, maribavir, and a pharmaceutically acceptable excipient or carrier, wherein the pharmaceutical composition provides a synergistic antiviral effect, optionally wherein the viral infection is a herpesvirus.

15. The method of claim 14, wherein the treating comprises suppressing or inhibiting viral infection; suppressing or inhibiting viral replication; prevention and/or prophylaxis of the viral infection; preventing maternal fetal transmission; preventing/or treating congenital infection; and reducing, inhibiting, or preventing viral spread.

16. A kit comprising a pharmaceutical composition comprising artemisone, a pharmaceutical composition comprising maribavir, and instructions for use of said compositions in treating a viral infection.

* * * * *